US006331273B1

(12) United States Patent
Nova et al.

(10) Patent No.: US 6,331,273 B1
(45) Date of Patent: *Dec. 18, 2001

(54) REMOTELY PROGRAMMABLE MATRICES WITH MEMORIES

(75) Inventors: Michael P. Nova, Rancho Santa Fe; Andrew E. Senyei, San Juan Capistrano; Gary S. David, La Jolla, all of CA (US)

(73) Assignee: Discovery Partners International, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/473,660

(22) Filed: Jun. 7, 1995

Related U.S. Application Data

(63) Continuation-in-part of application No. 08/428,662, filed on Apr. 25, 1995.

(51) Int. Cl.$^7$ .......................... G01N 15/06; G01N 33/53; C12Q 1/68; A61K 38/00

(52) U.S. Cl. .................... 422/68.1; 422/50; 422/57; 422/58; 422/82.05; 422/99; 422/102; 422/104; 435/6; 435/5; 435/7.1; 435/7.2; 435/7.9; 435/91.1; 436/161; 436/501; 436/182; 436/183; 436/518; 436/578; 436/523; 436/528; 530/333; 530/334; 530/335; 530/388.1

(58) Field of Search ........................ 422/68.1, 50, 57, 422/58, 82.05, 99, 102, 104; 435/6, 7.1–7.9, 91.1, 5; 436/161, 501, 182, 183, 518, 578, 523–528; 365/163; 536/24.3–33; 530/333, 334, 388.1; 364/496–499; 257/225, 390; 395/430; 488/131

(56) References Cited

U.S. PATENT DOCUMENTS

| Re. 34,936 | 5/1995 | Campbell et al. ............ 606/117 |
|---|---|---|
| 3,119,099 | 1/1964 | Biernat ........................ 365/151 |
| 3,692,498 | 9/1972 | Frank et al. ..................... 23/292 |
| 3,704,952 | 12/1972 | Bird ............................... 356/87 |
| 3,781,120 | 12/1973 | Engelhardt ..................... 356/244 |
| 3,843,443 | 10/1974 | Fishman ........................ 195/63 |
| 3,867,517 | 2/1975 | Ling ............................... 424/1 |
| 3,920,124 | 11/1975 | Patterson ...................... 209/111.7 |
| 3,939,123 | 2/1976 | Matthews et al. .............. 260/77.5 |
| 4,006,117 | 2/1977 | Merrifield et al. .............. 260/45.9 |
| 4,006,403 | 2/1977 | Olsen et al. .................... 324/15 |
| 4,133,642 | 1/1979 | Nosaka et al. .................. 422/67 |
| 4,154,795 | 5/1979 | Thorne .......................... 422/99 |
| 4,162,355 | 7/1979 | Tsibris .......................... 526/293 |
| 4,171,412 | 10/1979 | Coupek et al. ................. 525/329 |
| 4,175,183 | 11/1979 | Ayers ............................ 536/57 |
| 4,177,038 | 12/1979 | Biebricher ....................... 8/192 |
| 4,178,439 | 12/1979 | Ayers et al. .................... 536/59 |
| 4,179,402 | 12/1979 | Kim et al. ...................... 252/431 |
| 4,180,524 | 12/1979 | Reusser et al. .................. 585/644 |
| 4,241,537 | 12/1980 | Wood ............................ 47/77 |
| 4,282,287 | 8/1981 | Giese ............................ 428/407 |
| 4,318,658 | 3/1982 | McIntyre ....................... 414/480 |
| 4,321,069 | 3/1982 | Ritter ............................ 55/161 |
| 4,333,072 | 6/1982 | Beigel ........................... 340/825.54 |
| 4,351,337 | 9/1982 | Sidman ......................... 128/260 |
| 4,376,110 | 3/1983 | David et al. ................... 436/513 |
| 4,424,579 | 1/1984 | Roesner ........................ 365/105 |
| 4,439,585 | 3/1984 | Gould et al. .................... 525/127 |
| 4,442,507 | 4/1984 | Roesner ........................ 365/100 |
| 4,450,150 | 5/1984 | Sidman ......................... 424/1.1 |
| 4,485,227 | 11/1984 | Fox ............................... 528/61 |
| 4,507,230 | 3/1985 | Tam et al. ...................... 260/112.5 |
| 4,530,840 | 7/1985 | Tice et al. ...................... 514/179 |
| 4,542,025 | 9/1985 | Tice et al. ...................... 424/78 |
| 4,542,102 | 9/1985 | Dattagupta et al. ............ 435/6 |
| 4,562,157 | 12/1985 | Lowe et al. .................... 435/291 |
| 4,569,981 | 2/1986 | Wenzel et al. ................. 528/67 |
| 4,588,880 | 5/1986 | Hesser .......................... 235/376 |
| 4,598,386 | 7/1986 | Roesner et al. ................ 365/105 |

(List continued on next page.)

FOREIGN PATENT DOCUMENTS

| 2344930 | 4/1974 | (DE) . |
|---|---|---|
| 9308204 | 8/1993 | (DE) . |
| 4310169 | 9/1993 | (DE) . |

(List continued on next page.)

OTHER PUBLICATIONS

Beck–Sickinger, et al., Semiautomated T–Bag peptide synthesis using 9–Fluorenyl–Methoxyearbonyl strategy and Benzotriazol–1–yl–Tetramethyl–Uronium Tetrafluoroborate activation, *Peptide Research*, 4(2):88–94, Mar. 1991–Apr. 1991.

(List continued on next page.)

*Primary Examiner*—Stephanie W. Zitomer
(74) *Attorney, Agent, or Firm*—Kilpatrick Stockton LLP

(57) ABSTRACT

Combinations, called matrices with memories, of matrix materials with remotely addressable or remotely programmable recording devices that contain at least one data storage unit are provided. The matrix materials are those that are used in as supports in solid phase chemical and biochemical syntheses, immunoassays and hybridization reactions. The data storage units are preferably non-volatile antifuse memories. By virtue of this combination, molecules and biological particles, such as phage and viral particles and cells, that are in proximity or in physical contact with the matrix combination can be labeled by programming the memory with identifying information and can be identified by retrieving the stored information. Combinations of matrix materials, memories, and linked molecules and biological materials are also provided. The combinations have a multiplicity of applications, including combinatorial chemistry, isolation and purification of target macromolecules, capture and detection of macromolecules for analytical purposes, selective removal of contaminants, enzymatic catalysis, chemical modification and other uses. Methods for electronically tagging molecules are biological particles and matrix support materials and immunoassays and and other methods are also provided.

19 Claims, 7 Drawing Sheets

U.S. PATENT DOCUMENTS

| | | | |
|---|---|---|---|
| 4,631,211 | 12/1986 | Houghten | 428/35 |
| 4,646,266 | 2/1987 | Ovshinsky et al. | 365/105 |
| 4,652,528 | 3/1987 | Domkowski | 436/56 |
| 4,654,512 | 3/1987 | Gardosi | 235/376 |
| 4,657,543 | 4/1987 | Langer et al. | 604/891 |
| 4,681,870 | 7/1987 | Balint, Jr. et al. | 502/403 |
| 4,683,202 | 7/1987 | Mullis | 435/91 |
| 4,702,732 | 10/1987 | Powers et al. | 604/20 |
| 4,705,503 | 11/1987 | Dorman et al. | 604/50 |
| 4,745,072 | 5/1988 | Elkins et al. | 435/500 |
| 4,762,881 | 8/1988 | Kauer | 525/54.11 |
| 4,777,019 | 10/1988 | Dandekar | 422/68 |
| 4,779,806 | 10/1988 | Langer et al. | 241/1 |
| 4,783,776 | 11/1988 | Ishigaki et al. | 369/109 |
| 4,786,277 | 11/1988 | Powers et al. | 604/20 |
| 4,791,285 | 12/1988 | Ohki | 235/449 |
| 4,796,074 | 1/1989 | Roesner | 357/51 |
| 4,807,140 | 2/1989 | Saulnier | 364/468 |
| 4,855,909 | 8/1989 | Vincent et al. | 364/413.01 |
| 4,857,893 | 8/1989 | Carroll | 340/572 |
| 4,870,574 | 9/1989 | Limisimaque | 364/300 |
| 4,876,668 * | 10/1989 | Thakoor et al. | 365/163 |
| 4,885,250 | 12/1989 | Eveleigh et al. | 435/181 |
| 4,889,800 | 12/1989 | Shinnick et al. | 435/7 |
| 4,908,405 | 3/1990 | Bayer et al. | 525/61 |
| 4,908,694 | 3/1990 | Hidaka et al. | 357/74 |
| 4,908,813 | 3/1990 | Ojima et al. | 369/94 |
| 4,927,879 | 5/1990 | Pidgeon | 525/54.1 |
| 4,931,498 | 6/1990 | Pidgeon | 525/54.1 |
| 4,933,285 | 6/1990 | Patton | 435/181 |
| 4,952,531 | 8/1990 | Cherukuri | 501/69 |
| 4,952,928 | 8/1990 | Carroll et al. | 340/825.54 |
| 4,954,444 | 9/1990 | Eveleigh et al. | 435/181 |
| 4,958,452 | 9/1990 | Tate | 40/301 |
| 4,960,983 | 10/1990 | Inoue | 235/449 |
| 4,973,493 | 11/1990 | Guire | 427/2 |
| 4,975,647 | 12/1990 | Downer et al. | 324/425 |
| 4,990,756 | 2/1991 | Hoeman | 235/462 |
| 4,991,719 | 2/1991 | Butcher et al. | 209/3.3 |
| 5,002,548 | 3/1991 | Campbell et al. | 606/116 |
| 5,004,606 | 4/1991 | Frincke et al. | 424/85.8 |
| 5,012,236 | 4/1991 | Troyk et al. | 340/825.54 |
| 5,024,727 | 6/1991 | Campbell et al. | 156/663 |
| 5,028,918 | 7/1991 | Giles et al. | 340/825.54 |
| 5,029,214 | 7/1991 | Hollander | 381/51 |
| 5,030,807 | 7/1991 | Landt et al. | 235/375 |
| 5,033,623 | 7/1991 | Grecksch et al. | 209/3.3 |
| 5,043,222 | 8/1991 | Cherukuri | 428/432 |
| 5,044,623 | 9/1991 | Munz et al. | 271/223 |
| 5,047,371 | 9/1991 | Cherukuri | 501/21 |
| 5,055,659 | 10/1991 | Hendrick et al. | 235/439 |
| 5,056,056 | 10/1991 | Gustin | 364/900 |
| 5,063,417 * | 11/1991 | Hopfield | 357/8 |
| 5,064,767 | 11/1991 | Le et al. | 436/89 |
| 5,073,703 | 12/1991 | Wehrmacher | 235/492 |
| 5,074,318 | 12/1991 | Campbell et al. | 128/899 |
| 5,087,570 | 2/1992 | Weissman et al. | 435/240.1 |
| 5,089,391 | 2/1992 | Buechler et al. | 435/7.1 |
| 5,089,877 | 2/1992 | Queyssac et al. | 357/70 |
| 5,092,992 | 3/1992 | Crane et al. | 210/198.2 |
| 5,095,362 | 3/1992 | Roesner | 357/23.4 |
| 5,099,226 | 3/1992 | Andrews | 340/572 |
| 5,100,626 | 3/1992 | Levin | 422/100 |
| 5,105,190 | 4/1992 | Kip et al. | 340/625.54 |
| 5,114,719 | 5/1992 | Sabel et al. | 424/422 |
| 5,119,163 | 6/1992 | Ishihara et al. | 357/51 |
| 5,120,642 | 6/1992 | Schlossman et al. | 435/7.24 |
| 5,120,662 | 6/1992 | Chan et al. | 436/530 |
| 5,121,748 | 6/1992 | Ditz et al. | 128/631 |
| 5,134,277 | 7/1992 | Yerbury et al. | 250/214 |
| 5,136,572 | 8/1992 | Bradley | 369/108 |
| 5,143,854 | 9/1992 | Pirrung et al. | 436/518 |
| 5,148,256 | 9/1992 | Potash | 357/45 |
| 5,148,404 | 9/1992 | Hilferink | 367/2 |
| 5,171,695 | 12/1992 | Elkins | 436/501 |
| 5,200,051 | 4/1993 | Cozzette et al. | 204/403 |
| 5,201,728 | 4/1993 | Giampapa | 604/891.1 |
| 5,211,165 | 5/1993 | Dumoulin et al. | 128/653.1 |
| 5,212,050 | 5/1993 | Mier et al. | 430/320 |
| 5,212,315 | 5/1993 | Jones et al. | 546/257 |
| 5,214,409 | 5/1993 | Beigel | 340/572 |
| 5,215,899 | 6/1993 | Dattagupta | 435/6 |
| 5,216,143 | 6/1993 | Hogan et al. | 536/24.32 |
| 5,217,870 | 6/1993 | Farah | 427/2 |
| 5,217,743 | 6/1993 | Hession et al. | 435/7.24 |
| 5,218,189 | 6/1993 | Hutchinson | 235/439 |
| 5,218,343 | 6/1993 | Stobbe et al. | 340/572 |
| 5,223,408 | 6/1993 | Goeddel et al. | 435/69.3 |
| 5,223,409 | 6/1993 | Ladner et al. | 435/69.7 |
| 5,228,001 | 7/1993 | Birge et al. | 356/215 |
| 5,232,831 | 8/1993 | Milliman et al. | 435/6 |
| 5,235,326 | 8/1993 | Beigel | 340/825.54 |
| 5,236,355 | 8/1993 | Brizzolara et al. | 433/80 |
| 5,242,974 | 9/1993 | Holmes et al. | 525/54.11 |
| 5,248,632 | 9/1993 | Tung et al. | 437/195 |
| 5,250,459 | 10/1993 | Lee | 437/52 |
| 5,250,944 | 10/1993 | Urbas et al. | 340/870.31 |
| 5,251,635 | 10/1993 | Dumoulin et al. | 128/653.1 |
| 5,252,743 | 10/1993 | Barrett et al. | 548/303.7 |
| 5,252,962 | 10/1993 | Urbas et al. | 340/870.17 |
| 5,253,198 | 10/1993 | Birge et al. | 365/106 |
| 5,255,680 | 10/1993 | Darrow et al. | 128/653.1 |
| 5,256,469 | 10/1993 | Cherukuri et al. | 428/210 |
| 5,257,011 | 10/1993 | Beigel | 340/572 |
| 5,258,289 | 11/1993 | Davis et al. | 435/69.6 |
| 5,260,203 | 11/1993 | Ladner et al. | 435/172.3 |
| 5,262,772 | 11/1993 | Urbas et al. | 340/825.54 |
| 5,265,610 | 11/1993 | Darrow et al. | 128/653.1 |
| 5,266,926 | 11/1993 | Beigel | 340/572 |
| 5,268,371 | 12/1993 | Mauclaire et al. | 514/185 |
| 5,270,170 | 12/1993 | Schatz et al. | 435/7.37 |
| 5,270,251 | 12/1993 | Cohen | 437/173 |
| 5,271,400 | 12/1993 | Dumoulin et al. | 128/653.2 |
| 5,272,666 | 12/1993 | Tsang et al. | 365/96 |
| 5,273,927 | 12/1993 | Gnadinger | 437/52 |
| 5,277,724 | 1/1994 | Prabhu | 156/89 |
| 5,282,158 | 1/1994 | Lee | 365/86 |
| 5,284,747 | 2/1994 | Milliman | 435/6 |
| 5,288,291 | 2/1994 | Teoh | 604/60 |
| 5,288,476 | 2/1994 | Pasqualini et al. | 424/1.65 |
| 5,288,514 | 2/1994 | Ellman | 427/2 |
| 5,288,622 | 2/1994 | Gray et al. | 435/69.4 |
| 5,290,734 | 3/1994 | Boardman et al. | 437/195 |
| 5,292,814 | 3/1994 | Bayer et al. | 525/243 |
| 5,292,874 | 3/1994 | Milliman | 536/24.32 |
| 5,296,122 | 3/1994 | Katsube et al. | 204/298.04 |
| 5,296,722 | 3/1994 | Potash | 257/50 |
| 5,300,278 | 4/1994 | Pasqualin et al. | 534/14 |
| 5,300,456 | 4/1994 | Tigelaar et al. | 437/195 |
| 5,304,498 | 4/1994 | Elkins | 436/501 |
| 5,306,466 | 4/1994 | Goldsmith | 422/58 |
| 5,307,808 | 5/1994 | Dumoulin et al. | 128/653.2 |
| 5,308,967 | 5/1994 | Jurisch | 235/492 |
| 5,310,686 | 5/1994 | Sawyers et al. | 436/518 |
| 5,311,039 | 5/1994 | Kimura et al. | 257/50 |
| 5,314,829 | 5/1994 | Coles | 436/165 |
| 5,316,922 | 5/1994 | Brown et al. | 435/69.7 |
| 5,316,971 | 5/1994 | Chiang et al. | 437/170 |
| 5,318,354 | 6/1994 | Tyler | 303/3 |
| 5,319,181 | 6/1994 | Shellhammer et al. | 235/462 |
| 5,322,812 | 6/1994 | Dixit et al. | 437/60 |

| Patent No. | Date | Inventor | Class |
|---|---|---|---|
| 5,323,704 | 6/1994 | Fraczek | 101/375 |
| 5,324,324 | 6/1994 | Vachon et al. | 607/120 |
| 5,324,483 | 6/1994 | Cody et al. | 422/131 |
| 5,324,591 | 6/1994 | Georger et al. | 428/552 |
| 5,324,633 | 6/1994 | Fodor et al. | 435/6 |
| 5,326,449 | 7/1994 | Cunningham | 204/403 |
| 5,326,696 | 7/1994 | Chang | 435/7.24 |
| 5,328,603 | 7/1994 | Velander et al. | 210/198.2 |
| 5,329,153 | 7/1994 | Dixit | 257/530 |
| 5,334,640 | 8/1994 | Desai et al. | 524/56 |
| 5,334,880 | 8/1994 | Abadeer et al. | 307/219 |
| 5,335,219 * | 8/1994 | Ovshinsky | 369/288 |
| 5,338,665 | 8/1994 | Schatz et al. | 435/6 |
| 5,342,772 | 8/1994 | Arenzen et al. | 435/181 |
| 5,346,789 | 9/1994 | Lewis et al. | 430/19 |
| 5,347,263 | 9/1994 | Carroll et al. | 340/572 |
| 5,347,283 | 9/1994 | Krizek et al. | 342/201 |
| 5,348,705 | 9/1994 | Koreyasu et al. | 422/67 |
| 5,348,867 | 9/1994 | Georgiou et al. | 435/69.7 |
| 5,349,173 | 9/1994 | Scheckel et al. | 235/492 |
| 5,350,645 | 9/1994 | Lake et al. | 429/124 |
| 5,351,052 | 9/1994 | D'Hont et al. | 342/42 |
| 5,352,579 | 10/1994 | Milliman | 435/6 |
| 5,353,795 | 10/1994 | Souza et al. | 128/653.2 |
| 5,359,115 | 10/1994 | Campbell et al. | 558/110 |
| 5,359,250 | 10/1994 | Toda | 310/313 |
| 5,361,385 * | 11/1994 | Bakalash | 395/124 |
| 5,362,899 | 11/1994 | Campbell | 558/108 |
| 5,364,797 | 11/1994 | Olson et al. | 436/501 |
| 5,366,733 | 11/1994 | Brizzolara et al. | 424/426 |
| 5,374,718 | 12/1994 | Hammond et al. | 536/24.32 |
| 5,377,678 | 1/1995 | Dumoulin et al. | 128/653.1 |
| 5,381,035 | 1/1995 | Chen et al. | 257/530 |
| 5,382,513 | 1/1995 | Lam et al. | 435/7.1 |
| 5,383,873 | 1/1995 | Hoey et al. | 604/891.1 |
| 5,384,028 | 1/1995 | Ito | 204/403 |
| 5,384,261 | 1/1995 | Wrinkler et al. | 436/518 |
| 5,384,481 | 1/1995 | Holzworth et al. | 257/530 |
| 5,386,024 | 1/1995 | Kacian et al. | 536/25.4 |
| 5,389,449 | 2/1995 | Afeyan et al. | 428/523 |
| 5,389,534 | 2/1995 | von Gentzkow et al. | 435/180 |
| 5,389,769 | 2/1995 | Yamashita et al. | 235/375 |
| 5,391,463 | 2/1995 | Ligler et al. | 430/272 |
| 5,395,587 | 3/1995 | Brigham-Burke et al. | 422/68.1 |
| 5,395,750 | 3/1995 | Dillon et al. | 435/5 |
| 5,397,939 | 3/1995 | Gordon et al. | 326/38 |
| 5,399,339 | 3/1995 | Pasqualini | 424/1.53 |
| 5,400,136 | 3/1995 | Vo-Dinh | 356/301 |
| 5,401,378 | 3/1995 | King et al. | 204/418 |
| 5,403,750 | 4/1995 | Braatz et al. | 436/531 |
| 5,405,783 | 4/1995 | Pirrung et al. | 436/518 |
| 5,408,037 | 4/1995 | Smith et al. | 530/308 |
| 5,410,155 | 4/1995 | Thomson et al. | 250/364 |
| 5,412,593 | 5/1995 | Magel et al. | 365/96 |
| 5,416,193 | 5/1995 | Desai | 530/334 |
| 5,416,486 | 5/1995 | Koert et al. | 342/42 |
| 5,420,328 | 5/1995 | Campbell | 558/110 |
| 5,420,579 | 5/1995 | Urbas et al. | 340/870.31 |
| 5,422,636 | 6/1995 | Urbas | 340/825.54 |
| 5,424,186 | 6/1995 | Fodor et al. | 435/6 |
| 5,432,018 | 7/1995 | Dower et al. | 435/5 |
| 5,435,937 | 7/1995 | Bell et al. | 252/301.18 |
| 5,437,277 | 8/1995 | Dumoulin | 128/653.1 |
| 5,438,439 | 8/1995 | Mok et al. | 359/10 |
| 5,440,511 | 8/1995 | Yamamoto et al. | 365/189.05 |
| 5,442,212 | 8/1995 | Eimori | 257/303 |
| 5,442,584 | 8/1995 | Jeong et al. | 365/149 |
| 5,442,940 | 8/1995 | Secker et al. | 128/670 |
| 5,443,066 | 8/1995 | Dumoulin | 128/653.1 |
| 5,443,816 | 8/1995 | Zamora et al. | 424/1.69 |
| 5,443,953 | 8/1995 | Hansen et al. | 424/1.49 |
| 5,445,150 | 8/1995 | Dumoulin et al. | 128/653.1 |
| 5,447,533 | 9/1995 | Vachon et al. | 607/120 |
| 5,449,941 | 9/1995 | Yamazaki et al. | 257/411 |
| 5,451,683 | 9/1995 | Barrett et al. | 548/302.7 |
| 5,451,896 | 9/1995 | Mori | 327/543 |
| 5,452,251 | 9/1995 | Akaogi et al. | 365/200 |
| 5,452,311 | 9/1995 | Wells et al. | 371/51.1 |
| 5,453,633 | 9/1995 | Yun | 257/306 |
| 5,457,184 | 10/1995 | Lehn et al. | 534/15 |
| 5,463,564 | 10/1995 | Agrafiotis et al. | 364/496 |
| 5,482,867 | 1/1996 | Barrett et al. | 438/518 |
| 5,489,678 | 2/1996 | Fodor et al. | 536/22.1 |
| 5,491,074 | 2/1996 | Aldwin et al. | 435/69.7 |
| 5,498,530 | 3/1996 | Schatz et al. | 435/69.1 |
| 5,503,805 | 4/1996 | Sugarman et al. | 422/131 |
| 5,527,681 | 6/1996 | Holmes | 435/6 |
| 5,541,061 | 7/1996 | Fodor et al. | 435/6 |
| 5,545,531 | 8/1996 | Rava et al. | 435/6 |
| 5,547,839 | 8/1996 | Dower et al. | 435/6 |
| 5,549,974 | 8/1996 | Holmes | 428/403 |
| 5,556,762 | 9/1996 | Pinilla et al. | 4351/7.21 |
| 5,565,324 | 10/1996 | Still et al. | 435/6 |
| 5,572,410 | 11/1996 | Gustafson | 361/807 |
| 5,583,819 | 12/1996 | Roesner et al. | 365/225.7 |
| 5,609,826 | 3/1997 | Cargill et al. | 422/99 |
| 5,641,634 | 6/1997 | Mandecki | 435/6 |

FOREIGN PATENT DOCUMENTS

| | | |
|---|---|---|
| 4213065 | 10/1993 | (DE). |
| 4313807 | 11/1993 | (DE). |
| 4301401 | 7/1994 | (DE). |
| 4306563 | 9/1994 | (DE). |
| 9416270 | 12/1994 | (DE). |
| 0196174 | 10/1986 | (EP). |
| 0378059 | 7/1990 | (EP). |
| 0410688 | 1/1991 | (EP). |
| 0420177 | 4/1991 | (EP). |
| 0526173 | 2/1993 | (EP). |
| 0535242 | 4/1993 | (EP). |
| 0541340 | 5/1993 | (EP). |
| 0554955 | 8/1993 | (EP). |
| 0569215 | 11/1993 | (EP). |
| 0637750 | 2/1995 | (EP). |
| 0640826 | 3/1995 | (EP). |
| 2110030 | 5/1972 | (FR). |
| 2526169 | 4/1983 | (FR). |
| 2555744 | 5/1985 | (FR). |
| 2306408 | 7/1997 | (GB). |
| 2306484 | 7/1997 | (GB). |
| 57016359 | 1/1981 | (JP). |
| 8401031 | 3/1984 | (WO). |
| 8603840 | 7/1986 | (WO). |
| 8801302 | 2/1988 | (WO). |
| 8901157 | 2/1989 | (WO). |
| 8908264 | 9/1989 | (WO). |
| 9015070 | 12/1990 | (WO). |
| 9201268 | 1/1992 | (WO). |
| 9207093 | 4/1992 | (WO). |
| 9209300 | 6/1992 | (WO). |
| 9210092 | 6/1992 | (WO). |
| 9213271 | 8/1992 | (WO). |
| 9306121 | 4/1993 | (WO). |
| 9308472 | 4/1993 | (WO). |
| 9413402 | 1/1994 | (WO). |
| 9402634 | 2/1994 | (WO). |
| 9405394 | 3/1994 | (WO). |
| 9408051 | 4/1994 | (WO). |
| 9411388 | 5/1994 | (WO). |
| 9413623 | 6/1994 | (WO). |
| 9414980 | 7/1994 | (WO). |
| 9417208 | 8/1994 | (WO). |

| | | |
|---|---|---|
| 9422889 | 10/1994 | (WO) . |
| 9426413 | 11/1994 | (WO) . |
| 9428424 | 12/1994 | (WO) . |
| 9500530 | 1/1995 | (WO) . |
| 9502566 | 1/1995 | (WO) . |
| WO 95/12808 * | 5/1995 | (WO) . |
| 9519567 | 7/1995 | (WO) . |
| 9623749 | 8/1996 | (WO) . |
| 9624061 | 8/1996 | (WO) . |
| 9714041 | 4/1997 | (WO) . |
| 9719958 | 6/1997 | (WO) . |
| 9720073 | 6/1997 | (WO) . |
| 9720074 | 6/1997 | (WO) . |

OTHER PUBLICATIONS

Dialog Abstract 000867978, citing: FR 2110030 (Undated).
Dialog Abstract 009968074, citing: DE 43 01401 A1 No Date.
Dialog Abstract 009659308, citing: DE 43 13807 A1 No Date.
Jurisch, Identifikation: kontaktlos via Hochfrequenz, Elektronik 9, pp. 86–92 (1993).
Dialog Abstract 003812858, citing: FR 2 526 169 No Date.
Dialog Abstract 004334295, citing: FR 2 555 744 No Date.
Dialog Abstract 008591601, citing: EP 420 177 A1 No Date.
Dialog Abstract 009619322, citing: DE 43 10169 A1 No Date.
Dialog Abstract 009652137, citing: DE 42 13 0659 A1 No Date.
Dialog Abstract 010012814, citing: DE 43 06 5639 A1 No Date.
Dialog Abstract 010692826, citing: DE 94 16 270 A1 No Date.
Dialog Abstract 010167274, citing: EP 637 750 A2 (Undated).
Brenner et al., Encoded combinatorial chemistry, *Proc. Natl. Acad. Sci. USA 89:* 5381–5383 (1992).
Houghten, General method for the rapid solid–phase synthesis of large numbers of peptides; Specificity of antigen–antibody interaction at the level of individual amino acids, *Proc. Natl. Acad. Sci. USA 82*: 5131 (1985).
"IUPAC–IUB Commission on Biochemical Nomenclature," *Biochem.,* 11(5):942–944 (1972).
Baum, "Combinatorial Approaches Provide Fresh Leads for Medicinal Chemistry," *C&EN,* pp. 20–26 (1994).
Clackson, et al., "Making antibody fragments using phage display libraries," *Nature,* 352:624–628 (1991).
Devlin, et al., "Random Peptide Libraries: A Source of Specific Protein Binding Molecules," *Science,* 249:404–406 (1990).
Dower & Fodor, "Chapter 28. The Search for Molecular Diversity (II): Recombinant and Synthetic Randomized Peptide Libraries," *Annu. Rep. Med. Chem.,* 26:271–280 (1991).
Ekins, et al., "Multinalyte Immunoassay: The Immunological 'Compact Disk' of the Future," *J. Clin. Immun.,* 13(4):169–181 (1990).
Gallop, et al., "Applications of Combinatorial Technologies to Drug Discovery. 1. Background and Peptide Combinatorial Libraries," *J. Med. Chem.,* 37(9):1233–1251 (1994).
Gordon, et al., "Applications of Combinatorial Technologies to Drug Discovery. 2. Combinatorial Organic Synthesis, Library Screening Strategies, and Future Directions," *J. Med. Chem.,* 37(10):1385–1401 (1994).

Janda, "Tagged versus untagged libraries: Methods for the generation and screening of combinatorial chemical libraries," *Proc. Natl. Acad. Sci. USA,* 91:10779–10785 (1994).
Jung, et al., "Multiple Peptide Synthesis Methods and Their Applications," *Angew. Chem. Int. Ed. Engl.,* 31(4):367–486 (1992).
Pavia, et al., "The Generation of Molecular Diversity," *Bioorg. & Med. Chem. Lett.,* 3(3):387–396 (1993).
Scott, et al., "Searching for Peptide Ligands with an Epitope Library," *Science,* 249:386–390 (1990).
Zuckermann, et al., "Identification of highest–affinity ligands by affinity selection from equimolar peptide mixtures generated by robotic synthesis," *Proc. Natl. Acad. Sci. USA,* 89:4505–4509 (1992).
Cwirla, et al., "Peptides on phage: A vast library of peptides for identifying ligands," *Proc. Natl. Acad. Sci. USA,* 87:6378–6382 (1990).
Kessler, "Peptoids—A New Approach to the Development of Pharmaceuticals," *Angew. Chem. Int. Ed. Engl.,* 32(4): 543–544 (1993).
Simon, et al., "Peptoids: A modular approach to drug discovery," *Proc. Natl. Acad. Sci. USA,* 89:9367–9371 (1992).
Fodor, et al., "Light–Directed, Spatially Addressable Parallel Chemical Synthesis," *Science* 251:767–773 (1991).
Houghten, et al., "The Use of Synthetic Peptide Combinatorial Libraries for the Identification of Bioactive Peptides," *BioTechniques* 13(3):412–421 (1992).
Houghten, et al., "Generation and use of synthetic peptide combinatorial libraries for basic research and drug discovery," *Nature* 354:84–86 (1991).
Lam, et al., "A new type of synthetic peptide library for identifying ligand–binding activity," *Nature* 354:82–83.
Spatola, "Peptide backbone modifications: A structure–activity analysis of peptides containing amide bond surrogates. Conformation constraints, and related backbone replacements," *Chem. Biochem. Amino Acids, Pept. Proteins,* 7:267–357 (1983).
Szelke, et al., "Novel Transition–state Analogue Inhibitors of Renin," In *Peptides: Structure and Function. Proceedings of the Eighth American Peptide Symposium,* pp. 579–582 (1983).
Zuckerman, et al., Efficient Method for the Preparation of Peptoids [Oligo(N–substituted glycines)] by Submonomer Solid–Phase Synthesis, *J. Am. Chem. Soc.* 114:10646–10647 (1992).
Zuckerman, et al., "Discovery of Nanomolar Ligands for 7–Transmembrane G–Protein–Coupled Receptors from a Diverse N–(Substituted)glycine Peptoid Library," *J. Med. Chem.* 37:2678–2685 (1994).
Brown, et al., "Modern machine–aided methods of oligodeoxyribonucleotide synthesis," *Oligonucleotides Analogues,* Eckstein, Fritz (Ed), IRL, Oxford, UK, pp. 1–24 (1991).
DeWitt, et al., "'Diversomers': An approach to nonpeptide, nonoligomeric chemical diversity," *Proc. Natl. Acad. Sci. USA,* 90:6909–6913 (1993).
Eichler and Houghten, "Identification of Substrate–Analog Trypsin Inhibitors through the Screening of Synthetic Peptide Combinatorial Libraries," *Biochem.,* 32:11035–11041 (1993).
Nogrady, "Pro–Drugs and soft Drugs," *Medicinal Chemistry: A Biochemical Approach,* Oxford Univ. Press, N.V., pp. 388–392 (1985).
Scott and Craig, "Random peptide libraries," *Biotech.,* 5:40–48 (1994).

Buechler, et al., "Simultaneous Detection of Seven Drugs of Abuse by the Triage™ Panel for Drugs of Abuse," *Clin. Chem.,* 38(9):1678–1684 (1992).

Butz, "Immunization and Affinity Purification of Antibodies Using Resin–Immobilized Lysine–Branched Synthetic Peptides," *Peptide Res.,* 7(1):20–23 (1994).

Ketner & Kelly, "Integrated simian virus 40 sequences in transformed cell DNA: Analysis using restriction endonucleases," *Proc. Nat. Acad. Sci. USA,* 73(4):1102–1106 (1976).

Southern, "Detection of Specific Sequences Among DNA Fragments Separated by Gel Electrophoresis," *J. Mol. Biol.,* 98:503–517 (1975).

Towbin, et al., "Electrophoretic transfer of proteins from polyacrylamide gels to nitrocellulose sheets: Procedure and some applications," *Proc. Natl. Acad. Sci. USA,* 76(9):4350–4354 (1979).

Bloom, "A Memory to Remember," *Electronics Systems Design Magazine,* pp. 5–9 (1989) (Best Copy Available Supplied).

Cohen, et al., "A Flat–Aluminum Based Voltage–Programmable Link for Field–Programmable Devices," *IEEE Transactions on Electron Devices,* 41(5):721–725 (1994).

Cook & Keller, "Amorrhous Silicon Antifuse Technology for Bipolar PROMS," *Proc. IEEE Bipolar Circuits Technol. Meet.,* pp. 99–100 (1986).

Greve, "Programming Mechanism of Polysilicon Resistor Fuses," *IEEE Transactions on Electron Devices,* ED–29(4):719–724 (1982).

Haarer, "Photochemical Hole Burning: A High Density Storage Scheme," Proc. Int. Symp. on Optical Memory, 1987; *Japanese Journal of Applied Physics,* vol. 26 (1987) Supplement 26–4, pp. 227–232.

Isailović, "Optical Memories," *Videodisc and Optical Memory Systems,* Prentice–Hall, Inc., pp. iii, 292–323 (1985).

Pein and Plummer, "A 3–D Sidewall Flash EPROM Cell and Memory Array," *IEEE Transcations on Electron Devices,* 40(11) (1993).

Pokrowsky, et al., "Reading and writing of photochemical holes using GaAIAs–diode lasers," *Optics Lett.,* 8(5):280–282 (1983).

Shacham–Diamand, et al., "IPEL—A Novel Ion–Implanted Electrically Programmable Element," *IEEE Electron Device Lett.,* 10(5):180–182 (1989).

Tanimoto, et al., "A Novel MOS PROM Using a Highly Resistive Poly–Si Resistor," *IEEE Transactions on Electron Devices,* ED–27(3):517–520 (1980).

Wild, et al., "Hole Burning, Stark–Effect and Holographic Image Storage," Proc. Int. Symp. on Optical Memory (1987), *Japanese Journal of Applied Physics,* vol. 26 (1987) Supplement 26–4, pp. 233–236.

Yoshimura, et al., "Ultra–High Density Optical Memory by Photochemical Hole Burning (PHB) and Multi–Layered PHB System," SPIE vol. 1078, Optical Data Storage Topical Meeting (1989).

Dave, et al., "Sol–Gel Encapsulation Methods for Biosensors," *Anal. Chem.,* 66(22):1120A–1127A (1994).

Piskin, et al., *Diagnostic Biosensor Polymers,* ACS Symposium Series No. 556, Chap. 18 (1994).

Usmani, *Diagnostic Biosensor Polymers,* ACS Symposium Series No. 556, pp. vii–x, 2–19 (1994).

Winquist and Danielsson, "Semiconductor field effect devices," *Biosensors. A Practical Approach,* Chap. 7, Cass, Ed., IRL Press at Oxford University Press, (1990).

Berg, et al., "Long–Chain Polystyrene–Grafted Polyethylene Film Matrix: A New Support for Solid–Phase Peptide Synthesis[1]," *J. Am. Chem. Soc.,* 111:8024–8026 (1989).

Berg, et al., "Peptide Synthesis on Polystyrene–Grafted Polyethylene Sheets," *Pept., Proc. Eur. Pept. Symp.,* 20th, Jung, G. et al. (Eds.), pp. 196–198.

Berg, et al., "Polystyrene–Grafted Polyethylene: Design of Film and Felt Matrices for Solid–Phase Peptide Synthesis," *Innovation Perspect. Solid Phase Synth. Collect. Pap.,* Int. Symp., 1st, Epton, Roger (Ed.), pp. 453–459 (1990).

Hermanson, et al., Chaps. 1 and 2, *Immobilized Affinity Ligand Techniques,* Academic Press, Inc. (1992).

Ito, et al., (Eds.), *Polymeric Materials for Microelectronic Applications: Science and Technology,* ACS Symposium Series No. 579, Chaps. 17, 23, 27–29, 35 and 36 (1995).

Kent and Merrifield, "Preparation and Properties of tert–Butyloxycarbonylaminoacyl–4–(oxymethyl)phenylacetamidomethyl–(Kel F–g–styrene) Resin, an Insoluble, Noncrosslinked Support for Solid Phase Peptide Synthesis," *Isr. J. Chem.,* 17:243–247 (1978).

Kleine, et al., "Lipopeptide–Polyoxyethylene Conjugates as Mitogens and Adjuvants," *Immunobiol.,* 190:53–66 (1994).

Merrifield, "Solid–Phase Peptide Synthesis. III. An Improved Synthesis of Bradykinin," *Biochemistry,* 3(9):1385–1390 (1964).

Mitchell, et al., "A New Synthetic Route to tert–Butyloxycarbonylaminoacyl–4–(oxymethyl)phenylacetamidomethyl–resin, an Improved Support for Solid–Phase Peptide Synthesis[1]," *J. Org. Chem.,* 43(14):2845–2852 (1978).

Mitchell, et al., "Preparation of Aminomethyl–Polystyrene Resin by Direct Amidomethylation," *Tetrahedron Lett.,* 42:3795–3798 (1976).

*Pierce Chemical Co. Catalog & Handbook* (1994), selected pages which describe the preparation of and use of such reagents and provides a commercial source for such reagents.

Johansson, et al., "Immobilized Enzymes in Microcalorimetry," *Methods in Enzymology,* 44:659–667 (1976).

Kennedy and Cabral, "Immobilized Enzymes," *Solid Phase Biochemistry, Analytical and Synthetic Aspects,* Scouten, Ed., 7:253–391 (1983).

Kwoh, et al., "Transcription–based amplification system and detection of amplified human immunodeficiency virus type 1 with a bead–based sandwich hybridization format," *Proc. Natl. Acad. Sci. USA,* 86:1173–1177 (1989).

Miles & Hales, "Labelled Antibodies and Immunological Assay Systems," *Nature,* 219:186–189 (1968).

Powers, et al., "Protein Purification by Affinity Binding to Unilamellar Vesicles," *Biotech. & Bioeng.,* 33:173–182 (1989).

Smith, et al., "Kinetically Inert Co(III) Linkage through an Engineered Metal Binding Site: Specific Orientation of Recombinant Human Papillomavirus Type 16 E7 Protein on a Solid Support," *Methods: A Companion to Methods in Enzymology,* 4:73–78 (1992).

Stewart and Young, *Solid Phase Peptide Synthesis,* 2d Edition, Pierce Chemical Co., pp. 53–73 (1984).

Wong, "Conjugation of Proteins to Solid Matrices," *Chemistry of Protein Conjugation and Cross Linking,* 12:295–317 (1993).

Burgess, et al., "Combinatorial technologies involving reiterative division/ coupling/ recombination: Statistical considerations," *J. Med. Chem.* 37:2985 (1994).

Mjalli and Toyonaga, "Solid support combinatorial chemistry in lead discovery and SAR optimization," *NetSci* 1(1) (1995).

Moran, et al., "A radio frequency tag encoded combinatorial library method for the discovery of cinnamate amide inhibitors of the protein tyrosine phosphatase PTP1B," 31st Annual American Chemical Society Western Regional Meeting & 4th Annual San Diego Biotech Exposition. 117 (Oct. 9, 1995).

Moran et al. (Nov. 1995) "Radio frequency Tag Encoded Combinatorial Library Method for the Discovery of Tripeptide-Substituted Cinnamic Acid Inhibitors of the Protein Tyrosine Phosphatase PTP1B," *J. Am. Chem. Soc.* 117:10787–10788.

Nicolaou et al., "Radiofrequency Encoded Combinatorial Chemistry," *Agnew. Chem.* 34: 2289–2291 (Oct. 1995) (German version Radiofrequenz–verschlüsselte kombinatorische Chemie, *Agnew. Chem.* 107(20):2476–2479 (1995).

Article in *Scrip*, Dec. 15, 1995, p. 11, "New US combinatorial Company.".

Service, "Memory enhanced microreactor chemistry," *Science* 270:577 (1995).

Toyanaga et al., "Application of Solid Phase Synthesized Small Molecules Libraries in Drug Discovery." Abstract presented Tues., Nov. 7, 1995, at the First Annual Conference of The Society for BioMolecular Screening, (1995).

Barany, et al., "Solid–phase peptide synthesis: a silver anniversary report," *Int. J. Peptide Protein Res.* 30:705–739 (1987).

Furka, et al., "General method for rapid synthesis of multicomponent peptide mixtures," *Int. J. Pept. Protein Res.* 37:487–493 (1991).

Sebestyén, et al., "Chemical synthesis of peptide libraries," *Bioorg. Med. Chem. Lett.* 3:413–418 (1993).

Birge, "Photophysics and molecular electronic applications of the rhodpsins," *Ann. Rev. Phys. Chem* 41:683–733 (1990).

Ill, et al., "A COOH–terminal peptide confers regiospecific orientation and facilitates atomic force microscopy of an IgG$_1$," *Biophys J.* 64:919 (1993).

Kabat and Mayer, "Experimental Immunochemistry, Chapter 40. Equilibrium Dialysis," Charles C. Thomas, Springfield, Illinois. pp. 715–718 (1961).

Khrapko, et al., "An oligonucleotide hybridization approach to DNA sequencing," *FEBS Lttrs.* 256:118–122 (1989).

Sherwood, et al., "Controlled antibody delivery systems," *Bio/Technology* 10:1446–1449 (1992).

Bayer, et al., "New polymer supports for solid–liquid–phase synthesis," *Chem. Pept. Proteins* 3: 3–8 (1986).

Bayer, et al., "Polystyrene–immobilized PEG chains," *Poly-(Ethylene Glycol) Chem.* Harris, ed., pp. 325–345 (1992).

Bayer, et al., "New polymer and strategy for solid–phase synthesis of protected peptide fragments," In *Pept.: Chem., Struct. Biol., Proc. Am. Pept. Symp., 13th* Hodges, et al., Eds., pp. 156–158 (1994).

*Immobilized Biochemicals and Affinity Chromatography*, Part I, R. Bruce Dunlap, Ed., Plenum Press, N.Y. (1974).

Harlow, et al., *Antibodies. A Laboratory Manual*, Cold Spring Harbor Laboratory Chap. 14 (1988).

Ilg, et al., "Investigation of the diffusion process in cross–linked polystyrenes by means of NMR imaging and solid–state NMR spectroscopy," *Macromolecules*, pp. 2778–2783 (1994).

Gilham, *Immobilized Polynucleotides and Nucleic Acids*, pp. 173–185.

*Affinity Techniques. Enzyme Purification: Part B. Methods in Enzymology*, vol. 34, W. B. Jakoby, M. Wilchek, Eds., Acad. Press, N.Y. (1974).

Kaji, "Molecular Design of Epoxy Resins for Microelectronics Packaging," Chap. 17, American Chemical Society (1994).

Loetscher, et al., "Immobilization of monoclonal antibodies for affinity chromatography," *J. Chromatography* 595:113 (1992).

Nokihara, et al., "Superior support for solid–phase peptide synthesis," *Shimadzu Hyoron* 50:25–31 (1993).

Pidgeon, et al., "Solid phase membrane mimetics," *Enzyme Microb. Technol.* 12:149 (1990).

Rapp, et al., "Polystyrene–polyoxyethylene graftcopolymers for high speed peptide synthesis," *Pept., Proc. Eur. Pept. Symp., 20th,* Jung et al., eds.,pp. 199–201 (1989).

Rapp, et al., "Continuous flow peptide synthesis on PSPOE–graft copolymers," *Innovation Perspect. Solid Phase Synth. Collect. Pap., Int. Symp., 1st,* Epton, ed., pp. 205–210 (1990).

Rapp, et al., "Peptide screening and optimization by using monosized 25-µm tentacle microspheres," In *Pept. Chem. 1992, Proc. Jpn. Symp., 2nd,* Yanaihara, ed., pp. 7–10 (1992).

Sakakibara, *The Use of Hydrogen Fluoride in Peptide Chemistry*, Chap. 3, Institute for Protein Research, Osaka Univ., Osaka, Japan.

Rapp, et al., "Monosized 15 micron grafted microspheres for ultra high speed peptide synthesis," *Pept.: Chem. Biol., Proc. Am. Pept. Symp., 12th,* Smith et al., Eds., pp. 529–530 (1992).

*Immobilized Enzyme, Antigens, Antibodies and Peptides. Preparation and Characterization,* Howard H. Weetall, Ed., Marcel Dekker, Inc., N.Y. (1975).

Wright, et al., "Large scale synthesis of oligonucleotides via phosphoramidite nucleosides and a high loaded polystyrene support," *Tetrahedron Lett.* 34:3373–3376 (1993).

Zeppezauer, et al., "Hydrophilic polystyrene–polyoxyethylene graft polymer beads as carrier of antigenic peptides for in vivo and in vitro immunization techniques," *Z. Naturforsch., B: Chem. Sci.* 48:1801–1806 (1993).

Zhang, et al., "Scale–up continuous–flow peptide synthesis of a partial sequence of tyrosine kinase using tentacle polymers," *Pept. 1992, Proc. Eur. Pept. Symp., 22nd,* Schneider, et al., Eds. pp. 432–433 (1993).

Baldwin et al., Synthesis of a small molecule combinatorial library encoded with molecular tags, *J. Am. Chem. Soc.* 117:5588 (1995).

Borman, Combinatorial chemists focus on small molecules, molecular recognition, and automation, *Chem. &Engin. News,* pp. 29–54 (1996).

Brandt et al., High–throughput screening: An overview, 21–26 (1995).

Dulac et al., A novel family of genes encoding putative pheromone receptors in mammals, *Cell 83*:195–206 (1995).

Ecker and Crooke, Combinatorial Drug discovery: Which method will produce the greatest value? *Biotechnology 13*: 351–360 (1995).

Martin et al., Measuring diversity: Experimental design of combinatorial libraries for drug discovery, *J. Med. Chem.* 38:1431 (1995).

Radio frequency encoded combinatorial chemistry (RECC) kit (available at http://www.irori.com/products.html on May 24, 1996).

Xiang et al., A combinatorial approach to materials discovery, *Science* 268:1738–1740 (1995).

Campbell et al., A transition state analogue inhibitor combinatorial library, *J. Am. Chem. Soc.* 117:5381 (1995).

Geysen et al., Strategies for epitope analysis using peptide synthesis, *J. Immunol. Meth.* 102:259–274 (1987).

Maeji et al., Grafted supports used with the multipin method of peptide synthesis, *Reactive Polymers* 22:203–212 (1994).

Nikolaiev et al., Peptide–encoding for structure determination of nonsequencable polymers within libraries synthesized and tested on solid–phase supports, *Peptide Research* (1992).

Scott et al., Random peptide libraries, *Current Biology* 5:40–48 (1994).

Bunin et al., The combinatorial synthesis and chemical and biological evaluation of a 1,4–benzodiazepine library, *Proc. Natl. Acad. Sci. USA* 91:4708–4712 (1994).

Bunin et al., A general method for the solid–phase synthesis of 1,4–benzodiazepine derivatives, *J. Am. Chem. Soc.* 114:10997–10998 (1992).

Chen et al., 'Analogous' organic synthesis of small–compound libraries: Validation of combinatorial chemistry in small–molecule synthesis, *J. Am. Chem. Soc.* 116:2661–2662 (1994).

Czarnik et al., Parke–Davis' Diversomers™ technology: A practical approach to simultaneous, parallel organic synthesis, *Polym. Prepr. (Am. Chem. Soc., Div. Polym. Chem.)* 35(2):985 (1994).

DeWitt et al., Diversomers: An approach to nonpeptide nonoligomeric chemical diversity, *Proc. Natl. Acad. Sci. USA* 90:6909–6913 (1993).

DeWitt et al., Diversomers™ technology: Solid phase synthesis, automation, and integration for the generation of chemical diversity, *Drug Develop. Res.* 33:116–124 (1994).

Goldmacher et al., Photoactivation of toxin conjugates, *Bioconjugate Chem.* 3:104–107 (1992).

Hazum et al., A photocleavalble protecting group for the thiol function of cysteine, *Pept., Proc. Eur. Pept. Symp., 16th,* Brunfeldt, K (Ed), pp. 105–110 (1981).

Kick et al., Expedient method for the solid–phase synthesis of aspartic acid protease inhibitors directed toward the generation of libraries, *J. Med. Chem.* 38:1427 (1995).

Liskamp, Opportunities for new chemical libraries: Unnatural biopolymers and diversomers, *Agnew. Chem. Int. Ed. Engl.* 33(6):633–636 (1994).

Mitchell et al., tert–Butyloxycarbonylaminoacyl–4–(oxymethyl)phenylacetamidomethyl–resin, an Improved Support for Solid–Phase Peptide Synthesis, *J. Org. Chem.* 43(14):2845–2852 (1978).

Padwa et al., Intramolecular reorganization of some unsaturated 2H–azirines, *J. Org. Chem.* 41(3):543–549 (1976).

Padwa et al., Thermal arrangements of allyl substituted 2H–azirines to 3–azabicyclo[3.1.0]hex–2–enes, *J. Org. Chem.* 41(1):180–182 (1976).

Pátek et al., All–cis cyclopentane scaffolding for combinatorial solid phase synthesis of small non–peptide compounds, *Tetrahedron Lett.* 35:9169–9172 (1994).

Pátek et al., Solid–phase synthesis of "small" organic molecules based on thiazolidine scaffold, *Tetrahedron Lett.* 36(13):2227–2230 (1995).

Randolph et al., Major simplifications in oligosaccharide syntheses arising from a solid–phase based method: An application to the synthesis of the Lewis b antigen, *J. Am. Chem. Soc.* 117:5712–5719 (1995).

Stankovic et al., Diversomers™ libraries: A novel approach to chemical diversity, in *Innovation and Perspectives in Solid Phase Synthesis,* R. Epton, ed. (SPCC Ltd. Birmingham, 1993) pp. 391–396.

Sucholeiki, Solid–phase photochemical C–S Bond cleavage of thioethers—A New approach to the solid–phase production of non–peptide molecules, *Tetrahedron Lttrs.* 35:7307 (1994).

Vedejs et al., A method for mild photochemical oxidation: Conversion of phenacyl sulfides into carbonyl compounds, *J. Org. Chem.* 49:573–575 (1984).

Wang, Solid phase synthesis of protected peptides via photolytic cleavage of the α–methylphenacyl ester anchoring linkage, *J. Org. Chem.* 41(20):3258–3261 (1976).

Yen et al., Optically controlled ligand delivery, 1. Synthesis of water–soluble copolymers containing photocleavable bonds, *Makromol. Chem.* 190:69–82 (1989).

Devices would detect drugs in sweat, *NASATECH* (May 1996).

Gu et al., Cross–talk–limited storage capacity of volume holographic memory, Reprinted with permission from *J. Optical Soc. Am.,* vol. 9(11), pp. 1978–1983 (Nov. 1992), in *Selected Papers on Holographic Storage.*

Gu et al., Noise gratings formed during the multiple exposure schedule in photorefractive media, Reprinted with permission from *Optics Communications,* vol. 93, pp. 213–218 (1992), in *Selected Papers on Holographic Storage.*

Hong et al., Volume holographic memory systems: techniques and architectures, *Optical Engineering* 34(8):2193–2203 (1995).

Li et al., Three–dimensional holographic disks, *Applied Optics* 33(17):3764–3774 (1994).

Mok, Angle–multiplexed storage of 5000 holograms in lithium niobate, *Optics Lttrs.* 18(11):915–917 (1993).

Prabhu et al., Co–fired ceramic on metal multilayer circuit board technology for multichip module packaging, *Proc. .SPIE–Int. Soc. Opt. Eng.* (*Proc. 1992 Intl. Symposium on Microelectronics*) 1847:601–606 (1992).

Psaltis, Parallel optical memories, *Byte* pp. 179–182 (Sep. 1992).

Psaltis et al., Holographic memories, *Scientific American* pp. 70–76 (Nov. 1995).

Qiao et al., Electrical fixing of photorefractive holograms in $Sr_{0.75}Ba_{0.25}Nb_2O_6$, Reprinted with permission from *Optics Lttrs.,* vol. 18(12), pp. 1004–1006 (Jun. 1993), in *Selected Papers on Holographic Storage.*

Qiao et al., Sampled dynamic holographic memory, Reprinted with permission from *Optics Lttrs.,* vol. 17(19), pp. 1376–1378 (Oct. 1992), in *Selected Papers on Holographic Storage.*

Basch et al., Cell separation using positive immunoselective techniques, *J. Immunol. Meths.* 56:269–280 (1983).

Batra et al., Insertion of constant region domains of human $IgG_1$ into CD4–PE40 increases its plasma half–life, *Molecular Immunol.* 30(4):379–386 (1993).

Bayer et al., in *Pept.: Struct. Funct., Proc. Am. Pept. Symp, 8th,* Hruby et al., Eds., pp. 87–90 (1983).

Boldt, Fractionation of human lymphocytes with plant lectins. II. *Lens culinaris* lection and wheat germ agglutinin identify distinct lymphocyte subclasses, *J. Immunol.* 123(2):808–816 (1979).

Dormán et al., Benzophenone photophores in biochemistry, *Biochemistry* 33(19):5661–5673 (1994).

Dunlap, ed., *Immobilized Biochemicals and Affinity Chromatography, Symposium on Affinity Chromatography and Immobilized Biochemicals,* Charleston, SC, 1973, Plenum Press, NY (1974).

Freshney, *Culture of Animal Cells. A Manual of Basic Technique,* Alan R. Liss, Inc., New York, pp. 141–143, 217–224 (1983).

Ishikawa et al., Enzyme–labeling of antibodies and their fragments for enzyme immunoassay and immunohistochemical staining, *J. Immunoassay* 4(3):209–327 (1983).

Loetscher et al., Immobilization of monoclonal antibodies for affinity chromatography using a chelating peptide, *J. Chromatography* 595:113–119 (1992).

Hale, Irreversible, oriented immobilization of antibodies to cobalt–iminodiacetate resin for use as immunoaffinity media, *Analytical Biochem.* 231:46–49 (1995).

Kleinman et al., Use of extracellular matrix components for cell culture, *Analytical Biochem.* 166:1–13 (1987).

Mage et al., Mouse lymphocytes with and without surface immunoglobulin: Preparative scale separation in polystyrene tissue culture dishes coated with specifically purified anti–immunoglobulin, *J. Immunol. Methods* 15:47–56 (1977).

Mage et al., Preparative nonlytic separation of $Lyt2^+$ and $Lyt2^-$ T lymphocytes, functional analyses of the separated cells and demonstration of synergy in graft–vs.–host reaction of $Lyt2^+$ and $Lyt2^-$ cells, *Eur. J. Immunol.* 11:228–235 (1981).

McKeehan et al., Stimulation of clonal growth of normal fibroblasts with substrata coated with basic polymers, *J. Cell Biol.* 71:727–734 (1976).

Padwa et al., Photocycloaddition of arylazirenes with electron–deficient olefins, *J. Am. Chem. Soc.* 93(2):548–550 (1971).

Senter et al., Novel photocleavable protein crosslinking reagents and thier use in the preparation of antibody–toxin conjugates, *Photochem. Photobiol.* 42(3):231–237 (1985).

Thiele et al., The immunosuppressive activity of L–leucyl–L–leucine methyl ester: Selective ablation of cytotoxic lymphocytes and monocytes, *J. Immunoassay* 136(3):1038–1048 (1986).

Tsao et al., Clonal growth of normal human epidermal keratinocytes in a defined medium, *J. Cell. Physiol.* 110:219–229 (1982).

Wysocki et al., 'Panning' for lymphocytes: A method for cell seclection, *Proc. Natl. Acad. Sci. USA* 75(6):2844–2848 (1978).

\* cited by examiner

REMOTELY PROGRAMMABLE MATRICES WITH MEMORIES

RELATED APPLICATIONS

This application is a continuation-in-part of U.S. application Ser. No. 08/428,662, filed Apr. 25, 1995, by Michael P. Nova and Andrew E. Senyei, entitled, "REMOTELY PROGRAMMABLE MATRICES WITH MEMORIES". The subject matter of U.S. application Ser. No. 08/428,662 is herein incorporated by reference in its entirety. The subject matter of U.S. application Ser. No. 08/480,196 entitled "REMOTELY PROGRAMMABLE MATRICES WITH MEMORIES" filed Jun. 7, 1995 by Michael P. Nova, Andrew E. Senyei and Gary S. David is also incorporated herein by reference thereto.

FIELD OF THE INVENTION

The present invention relates to the application of data storage technology to molecular tracking and identification. In particular, combinations of matrix materials with programmable data storage or recording devices, herein referred to as memories, are provided. By virtue of this combination, molecules and biological particles, such as phage and viral particles and cells, that are in proximity to or in physical contact with the matrix combination can be electromagnetically tagged by programming the memory with data corresponding to identifying information. The molecules and biological particles can be identified by retrieving the stored data points. Combinations of matrix materials, memories, and linked or proximate molecules and biological materials are also provided. The combinations provided herein have a multiplicity of applications, including combinatorial chemistry, isolation and purification of target macromolecules, capture and detection of macromolecules for analytical purposes, high throughput screening, selective removal of contaminants, enzymatic catalysis, chemical modification and other uses. These combinations are particularly advantageous for use in multianalyte analyses.

BACKGROUND OF THE INVENTION

There has been a convergence of progress in chemistry and biology. Among the important advances resulting from this convergence is the development of methods for generating molecular diversity and for detecting and quantifying small quantities of biological or chemical material. This advance been facilitated by fundamental developments in chemistry, including the development of highly sensitive analytical methods, solid state chemical synthesis, and sensitive and specific biological assay systems.

Analyses of biological interactions and chemical reactions, however, require the use of labels or tags to track and identify the results of such analyses. Typically biological reactions are monitored by radiolabels or direct or indirect enzyme labels. Chemical reactions are also monitored by direct or indirect means, such by linking the reactions to a second reaction in which a colored, fluorescent, chemiluminescent or other such product results. These analytical methods, however, are often time consuming and tedious. There is, thus, a need to develop alternative methods for tracking and identifying analytes in biological interactions and the reactants and products of chemical reactions.

Hybridization reactions

For example, it is often desirable to detect or quantify very small concentrations of nucleic acids in biological samples. Typically, to perform such measurements, the nucleic acid in the sample [i.e., the target nucleic acid] is hybridized to a detection oligonucleotide. In order to obtain a detectable signal proportional to the concentration of the target nucleic acid, either the target nucleic acid in the sample or the detection oligonucleotide is associated with a signal generating reporter element, such as a radioactive atom, a chromogenic or fluorogenic molecule, or an enzyme [such as alkaline phosphatase] that catalyzes a reaction that produces a detectable product. Numerous methods are available for detecting and quantifying the signal.

Following hybridization of a detection oligonucleotide with a target, the resulting signal-generating hybrid molecules must be separated from unreacted target and detection oligonucleotides. In order to do so, many of the commonly used assays immobilize the target nucleic acids or detection oligonucleotides on solid supports. Presently available solid supports to which oligonucleotides are linked include nitrocellulose or nylon membranes, activated agarose supports, diazotized cellulose supports and non-porous polystyrene latex solid microspheres. Linkage to a solid support permits fractionation and subsequent identification of the hybridized nucleic acids, since the target nucleic acid may be directly captured by oligonucleotides immobilized on solid supports. More frequently, so-called "sandwich" hybridization systems are used. These systems employ a capture oligonucleotide covalently or otherwise attached to a solid support for capturing detection oligonucleotide-target nucleic acid adducts formed in solution [see, e., EP 276,302 and Gingeras et al. (1989) *Proc. Natl. Acad. Sci. USA* 86:11 73]. Solid supports with linked oligonucleotides are also used in methods of affinity purification. Following hybridization or affinity purification, however, if identification of the linked molecule or biological material is required, the resulting complexes or hybrids or compounds must be subjected to analyses, such as sequencing.

Immunoassays

Immunoassays also detect or quantify very small concentrations of analytes in biological samples. Many immunoassays utilize solid supports in which antigen or antibody is covalently, non-covalently, or otherwise, such as via a linker, attached to a solid support matrix. The support-bound antigen or antibody is then used as an analyte in the assay. As with nucleic acid analysis, the resulting antibody-antigen complexes or other complexes, depending upon the format used, rely on radiolabels or enzyme labels to detect such complexes.

The use of antibodies to detect and/or quantitate reagents ["antigens"] in blood or other body fluids has been widely practiced for many years. Two methods have been most broadly adopted. The first such procedure is the competitive binding assay, in which conditions of limiting antibody are established such that only a fraction [usually 30–50%] of a labeled [e.g., radioisotope, fluorophore or enzyme] antigen can bind to the amount of antibody in the assay medium. Under those conditions, the addition of unlabeled antigen [eg., in a serum sample to be tested] then competes with the labeled antigen for the limiting antibody binding sites and reduces the amount of labeled antigen that can bind. The degree to which the labeled antigen is able to bind is inversely proportional to the amount of unlabeled antigen present. By separating the antibody-bound from the unbound labeled antigen and then determining the amount of labeled reagent present, the amount of unlabeled antigen in the sample [e.g., serum] can be determined.

As an alternative to the competitive binding assay, in the labeled antibody, or "immunometric" assay [also known as "sandwich" assay], an antigen present in the assay fluid is specifically bound to a solid substrate and the amount of antigen bound is then detected by a labeled antibody [see, e.g., Miles et al. (1968) *Nature* 29:186–189; U.S. Pat. No. 3,867,517; U.S. Pat. No. 4,376,110]. Using monoclonal antibodies two-site immunometric assays are available [see, e.g., U.S. Pat. No. 4,376,110]. The "sandwich" assay has been broadly adopted in clinical medicine. With increasing interest in "panels" of diagnostic tests, in which a number of different antigens in a fluid are measured, the need to carry out each immunoassay separately becomes a serious limitation of current quantitative assay technology.

Some semi-quantitative detection systems have been developed [see, e.g., Buechler et al. (1992) *Clin. Chem.* 38:1678–1684; and U.S. Pat. No. 5,089,391] for use with immunoassays, but no good technologies yet exist to carefully quantitate a large number of analytes simultaneously [see, e.g., Ekins et al. (1990) *J. Clin. Immunoassay* 13:169–181] or to rapidly and conveniently track, identify and quantitate detected analytes.

Combinatorial Libraries

Drug discovery relies on the ability to identify compounds that interact with a selected target, such as cells, an antibody, receptor, enzyme, transcription factor or the like. Traditional drug discovery involves screening natural products from various sources, or random screening of archived synthetic material. The current trend, however, is to identify such molecules by rational design and/or by screening combinatorial libraries of molecules.

Methods and strategies for generating diverse libraries, primarily peptide- and nucleotide-based oligomer libraries, have been developed using molecular biology methods and/or simultaneous chemical synthesis methodologies [see, e.g., Dower et al. (1991) *Annu. Rep. Med. Chem.* 26:271–280; Fodor et al. (1991) *Science* 251:767–773; Jung et al. (1992) *Angew. Chem. Ind. Ed. Engl.* 31:367–383; Zuckerman et al. (1992) *Proc. Natl. Acad. Sci. USA* 89:4505–4509; Scott et al. (1990) *Science* 249:386–390; Devlin et al. (1990) *Science* 249:404–406; Cwirla et al. (1990) *Proc. Natl. Acad. Sci. USA* 87:6378–6382; and Gallop et al. (1994) *J. Medicinal Chemistry* 37:1233–1251]. The resulting combinatorial libraries potentially contain millions of pharmaceutically relevant compounds and can be rapidly screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads [see, e.g., Lam et al. (1991) *Nature* 354:82–84] and cotton supports [see, e.g., Eichler et al. (1993) *Biochemistry* 32:11035–11041]; and methods in which the compounds are used in solution [see, e.g., Houghten et al. (1991) *Nature* 354:84–86, Houghten et al. (1992) *BioTechniques* 313:41 2–421; and Scott et al. (1994) *Curr. Opin. Biotechnol.* 5:40–48]. There are numerous examples of synthetic peptide and oligonucleotide combinatorial libraries. The present direction in this area is to produce combinatorial libraries that contain non-peptidic small organic molecules. Such libraries are based on either a basis set of monomers that can be combined to form mixtures of diverse organic molecules or that can be combined to form a library based upon a selected pharmacophore monomer.

There are three critical aspects in any combinatorial library: (i) the chemical units of which the library is composed; (ii) generation and categorization of the library, and (iii) identification of library members that interact with the target of interest, and keeping track of intermediary synthesis products and the multitude of molecules in a single vessel.

The generation of such libraries often relies on the use of solid phase synthesis methods, as well as solution phase methods, to produce combinatorial libraries containing tens of millions of compounds that can be screened in diagnostically or pharmacologically relevant in vitro assay systems. In generating large numbers of diverse molecules by step-wise synthesis, the resulting library is a complex mixture in which a particular compound is present at very low concentrations, so that it is difficult or impossible to determine its chemical structure. Various methods exist for ordered synthesis by sequential addition of particular moieties, or by identifying molecules based on spacial positioning on a chip. These methods are cumbersome and ultimately impossible to apply to highly diverse and large libraries.

Thus, an essential element of the combinatorial discovery process, as well as other areas in which molecules are identified and tracked, is the ability to extract the information made available during synthesis of the library or identification of the active components of intermediary structures. While there are several techniques for identification of intermediary products and final products, nanosequencing protocols that provide exact structures are only applicable on mass to naturally occurring linear oligomers such as peptides and amino acids. Mass spectrographic [MS] analysis is sufficiently sensitive to determine the exact mass and fragmentation patterns of individual synthesis steps, but complex analytical mass spectrographic strategies are not readily automated nor conveniently performed. Also, mass spectrographic analysis provides at best simple connectivity information, but no stereoisomeric information, and generally cannot discriminate among isomeric monomers. Another problem with mass spectrographic analysis is that it requires pure compounds; structural determinations on complex mixtures is either difficult or impossible. Finally, mass spectrographic analysis is tedious and time consuming. Thus, although there are a multitude of solutions to the generation of libraries, there are no ideal solutions to the problems of identification, tracking and categorization.

Similar problems arise in any screening or analytical process in which large numbers of molecules or biological entities are screened. In any system, once a desired molecule (s) has been isolated, it must be identified. Simple means for identification do not exist. Because of the problems inherent in any labeling procedure, it would be desirable to have alternative means for tracking and quantitating chemical and biological reactions during synthesis and/or screening processes.

Therefore, it is an object herein to provide methods for identification, tracking and categorization of the components of complex mixtures of diverse molecules.

SUMMARY OF THE INVENTION

Combinations of (i) a miniature recording device that contains one or more programmable data storage devices [memories] that can be remotely programmed and read; and (ii) a matrix, such as a particulate support used in chemical syntheses, are provided. The remote programming and reading is preferably effected using electromagnetic radiation.

The matrix materials [matrices] are any materials that are routinely used in chemical and biochemical synthesis. The matrix materials are typically polymeric materials that are compatible with chemical and biological syntheses and assays, and include/glasses, silicates, celluloses, polystyrenes, polysaccharides, sand, and synthetic resins and polymers, including acrylamides, particularly cross-linked polymers, cotton, and other such materials. The matrices may be in the form of particles or may be continuous in design, such as a test tube or microtiter plate or the like.

The recording device is a miniature device, typically less than 10 mm$^3$ in size, preferably smaller, that includes at least one data storage unit that includes a remotely programmable and remotely readable, preferably non-volatile, memory. This device with remotely programmable memory is in proximity with or in contact with the matrix. In particular, the recording device includes a memory device, preferably having non-volatile memory means, for storing a plurality of data points and means for receiving a transmitted signal that is received by the device and for causing a data point corresponding to the data signal to be permanently stored within the memory means; and, if needed, a shell that is non-reactive with and impervious to any processing steps or solutions in which the combination of matrix with recording device is placed, and that is transmissive of read or write signals transmitted to the memory. The device may also include at least one support matrix disposed on an outer surface of the shell for retaining molecules or biological particles.

The recording device [containing the memory] is typically coated with at least one layer of material, such as a protective polymer or a glass, including polystyrene, heavy metal-free glass, plastic, ceramic, and may be coated with more than one layers of this and other materials. For example, it may be coated with a ceramic or glass, which is then coated with or linked to the matrix material. Alternatively, the glass or ceramic or other coating may serve as the matrix.

The data storage device or memory is programmed with or encoded with information that identifies molecules or biological particles, either by their process of preparation, their identity, their batch number, category, physical or chemical properties, combinations of any of such information, or other such identifying information. The molecules or biological particles are in physical contact, direct or indirect, or in proximity with the matrix, which in turn is in physical contact or in the proximity of the recording device that contains the data storage memory. Typically, the matrix is on the surface of the recording device and the molecules and biological particles are in physical contact with the matrix material.

The matrix combinations, thus, contain a matrix material, typically in particulate form, in physical contact with a tiny device containing one or more remotely programmable data storage units [memories]. Contact can be effected by placing the recording device with memory on or in the matrix material or in a solution that is in contact with the matrix material or by linking the device, either by direct or indirect covalent or non-covalent interactions, chemical linkages or by other interactions, to the matrix.

For example, such contact is effected chemically, by chemically coupling the device with data storage unit to the matrix, or physically by coating the recording device with the matrix material or another material, by physically inserting or encasing the device in the matrix material, by placing the device onto the matrix or by any other means by which the device can be placed in contact with or in proximity to the matrix material.

Thus, combinations of a miniature recording device that contains or is a data storage unit linked to or in proximity with matrices or supports used in chemical and biotechnical applications, such as combinatorial chemistry, peptide synthesis, nucleic acid synthesis, nucleic acid amplification methods, organic template chemistry, nucleic acid sequencing, screening for drugs, particularly high throughput screening, phage display screening, cell sorting, tracking of biological particles and other such methods, are provided. These combinations of matrix material with data storage unit [or recording device including the unit] are herein referred to as matrices with memories.

The matrices are either particulate of a size that is roughly 10 mm$^3$ or smaller, typically 1 mm$^3$ or smaller, or a continuous medium, such as a microtiter plate or well or plastic or other solid polymeric vial or glass vial. In instances in which the matrix is continuous, the data storage device [memory] may be placed in or on the matrix medium or may be embedded in the material of the matrix. More than one data storage device may be in proximity to or contact with a matrix particle. For example, microtiter plates with the recording device containing the data storage unit [remotely programmable memory] embedded in each well or vials [typically with a 1 ml or smaller capacity] with an embedded recording device, may be manufactured. In other embodiments, the memory device may be linked to or in proximity to more than one matrix particle.

The combination of matrix with memory is used by contacting it with, linking it to, or placing it in proximity with a molecule or biological particle, such as a virus or phage particle, a bacterium or a cell, to produce a second combination of a matrix with memory and a molecule or biological particle. In certain instances, such combinations of matrix with memory or combination of matrix with memory and molecule or biological particle may be prepared when used or may be prepared before use and packaged or stored as such for future use.

Since matrix materials have many known uses in conjunction with molecules and biological particles, there are a multitude of methods known to artisans of skill in this art for linking, joining or physically contacting the molecule or biological particle with the matrix material. In some embodiments, the recording device with data storage unit is placed in a solution or suspension of the molecule or biological particle of interest. In such instances, the container, such as the microtiter plate or test tube or other vial, is the matrix material. The recording device is placed in or on the matrix or can be embedded, encased or dipped in the matrix material.

The miniature recording device containing the data storage unit(s) with remotely programmable memory, includes, in addition to the remotely programmable memory, means for receiving information for storage in the memory and for retrieving information stored in the memory. Such means is typically an antenna, which also serves to provide power, that can be tuned to a desired electromagnetic frequency to program the memory. Preferred frequencies are any that do not substantially alter the molecular biological interactions of interest, such as those that are not substantially absorbed by the molecules or biological particles linked to the matrix or in proximity of the matrix, and that do not alter the support properties of the matrix. Radio frequencies are presently preferred, but other frequencies or optical lasers will be used, as long as the selected frequency or optical laser does not interfere with the interactions of the molecules or biological particles of interest. Thus, information in the form of data points corresponding to such information is stored in and retrieved from the data storage device by application of a selected electromagnetic radiation frequency.

The preferred miniature recording device for use in the combinations herein is a single substrate of a size preferably less than about 10 mm$^3$, that includes a remotely programmable data storage unit(s) [memory], preferably a non-volatile memory, and an antenna for receiving or transmitting an electromagnetic signal, preferably a radio frequency signal; the antenna, memory and other components are preferably provided on a single substrate, thereby minimizing the size of the device. The device is preferably smaller than 10 mm$^3$ in volume, more preferably less than 5 mm$^3$, most preferably about 1 mm$^3$ or smaller, and is rapidly programmable, preferably in less than 5 seconds, more preferably in about 1 second, and most preferably in about 1 millisecond or less. The preferred memory is non-volatile, permanent, and relies on antifuse circuitry.

Containers, such as vials, tubes, microtiter plates, and the like, which are in contact with a recording device that contains a data storage unit with programmable memory are also provided. The container is typically of a size used in immunoassays or hybridization reactions, generally a liter or less, typically less than 100 ml, and often less than about 10 ml in volume. Alternatively the container can be in the form of a plurality of wells, such as a microtiter plate, each well having about 1 ml or less in volume. The container is transmissive to the electromagnetic radiation, such as radio frequencies, infrared wavelengths, ultraviolet wavelengths, microwave frequencies, visible wavelengths, X-rays or laser light, used to program the recording device.

Methods for electromagnetically tagging molecules or biological particles are provided. Such tagging is effected by placing the molecules or biological particles of interest in proximity with the recording device or with the matrix with memory, and programming or encoding the identity of the molecule or synthetic history of the molecules or batch number or other identifying information into the memory. The, thus-identified molecule or biological particle is then used in the reaction or assay of interest and tracked by virtue of its linkage to the matrix with memory or its proximity to the matrix with memory, which can be queried to identify the molecule or biological particle. The tagging and/or reaction or assay protocols may be automated.

In particular, methods for tagging constituent members of combinatorial libraries and other libraries or mixtures of diverse molecules and biological particles are provided. These methods involve electromagnetically tagging molecules, particularly constituent members of a library, by contacting the molecules or biological particles or bringing such molecules or particles into proximity with a matrix with memory and programming the memory with retrievable information from which the identity, synthesis history, batch number or other identifying information can be retrieved. The contact is preferably effected by coating, completely or in part, the recording device with memory with the matrix and then linking, directly or via linkers, the molecule or biological particle of interest to the matrix support. The memories can be coated with a protective coating, such as a glass or silicon, which can be readily derivatized for chemical linkage or coupling to the matrix material. In other embodiments, the memories can be coated with matrix, such as for example dipping the memory into the polymer prior to polymerization, and allowing the polymer to polymerize on the surface of the memory.

If the matrices are used for the synthesis of the constituent molecules, the memory of each particle is addressed and the identity of the added component is encoded in the memory at [before, during, or preferably after] each step in the synthesis. At the end of the synthesis, the memory contains a retrievable record of all of the constituents of the resulting molecule, which can then be used, either linked to the support, or following cleavage from the support in an assay or for screening or other such application. If the molecule is cleaved from the support with memory, the memory must remain in proximity to the molecule or must in some manner be traceable to the molecule. Such synthetic steps may be automated.

In preferred embodiments, the matrix with memory with linked molecules [or biological particles] are mixed and reacted with a sample according to a screening or assay protocol, and those that react are isolated. The identity of reacted molecules can then be ascertained by remotely retrieving the information stored in the memory and decoding it identify the linked molecules.

Compositions containing combinations of matrices with memories and compositions of matrices with memories and molecules or biological particles are also provided. In particular, coded or electronically tagged libraries of oligonucleotides, peptides, proteins, non-peptide organic molecules, phage display, viruses and cells are provided. Particulate matrices, such as polystyrene beads, with attached memories, and continuous matrices, such as microtiter plates or slabs, with a plurality of embedded or attached memories are provided.

These combinations of matrix materials with memories and combinations of matrices with memories and molecules or biological particles may be used in any application in which support-bound molecules or biological particles are used. Such applications include, but are not limited to diagnostics, such as immunoassays, drug screening assays, combinatorial chemistry protocols and other such uses. These matrices with memories can be used to tag cells for uses in cell sorting, to identify molecules in combinatorial syntheses, to label monoclonal antibodies, to tag constituent members of phage displays, in affinity separation procedures, to label DNA and RNA, in nucleic acid amplification reactions [see, e.g., U.S. Pat. No. 5,403,484; U.S. Pat. No. 5,386,024; U.S. Pat. No. U.S. Pat. No. 4,683,202 and, for example International PCT Application WO/94 02634, which describes the use of solid supports in connection with nucleic acid amplification methods], to label known compounds, particularly mixtures of known compounds in multianalyte analyses], to thereby identify unknown compounds, or to label or track unknowns and thereby identify the unknown by virtue of reaction with a known. Thus, the matrices with memories are particularly suited for high throughput screening applications and for multianalyte analyses.

Systems and methods for recording and reading or retrieving the information in the data storage devices regarding the identity or synthesis of the molecules or biological particles are also provided. The systems for recording and reading data include: a host computer or other encoder/decoder instrument having a memory for storing data relating to the identity or synthesis of the molecules, and a transmitter means for receiving a data signal and generating a signal for transmitting a data signal; and a recording device that includes a remotely programmable, preferably non-volatile, memory and transmitter means for receiving a data signal and generating at least a transmitted signal and for providing a write signal to the memory in the recording device.

In particular, the systems include means for writing to and reading from the memory device to store and identify each of the indicators that identify or track the molecules and biological particles. The systems additionally include the matrix material in physical contact with or proximate to the recording device, and may also include a device for separating matrix particles with memory so that each particle or memory can be separately programmed.

Methods for tagging molecules and biological particles by contacting, either directly or indirectly, a molecule or biological particle with a recording device; transmitting from a host computer or decoder/encoder instrument to the device electromagnetic radiation representative of a data signal corresponding to an indicator that either specifies one of a series of synthetic steps or the identity or other information for identification of the molecule or biological particle, whereby the data point representing the indicator is written into the memory, are provided.

Methods for reading identifying information from recording devices linked to or in contact with or in proximity to a electromagnetically tagged molecule or electromagnetically tagged biological particles are provided. These methods include the step of exposing the recording device containing the memory in which the data is stored to electromagnetic radiation [EM]; and transmitting to a host computer or decoder/encoder instrument an indicator representative of a the identity of a molecule or biological particle or identification of the molecule or biological particle linked to or in proximity to the recording device.

One, two, three and N-dimensional arrays of the matrices with memories are also provided. Each memory is programmed with its position in the array. Such arrays may be used for blotting, if each matrix particle is coated on one at least one side with a suitable material, such as nitrocellulose. For blotting, each memory is coated on at least one side with the matrix material and arranged contiguously to adjacent memories to form a substantially continuous sheet. After blotting, the matrix particles may be separated and reacted with the analyte of interest, after which the physical position of the matrices to which analyte binds may be determined. The amount of bound analyte may also be quantified. Southern, Northern, Western and dot blot assays using such arrays are provided. Dimensions beyond can refer to additional unique identifying paramenters, such as batch number.

Immunoassays, such as enzyme linked immunosorbent assays [ELISAs] in which at least one analyte is linked to a solid support matrix that is combined with a recording device containing a data storage unit with a programmable, preferably remotely programmable and non-volatile, memory are provided.

Molecular libraries, such as phage display libraries, DNA libraries, in which the constituent molecules are combined with a solid support matrix that is combined with a data storage unit with a programmable memory are provided.

Affinity purification protocols in which the affinity resin is combined with a recording device containing a data storage unit with a programmable memory are also provided.

DETAILED DESCRIPTION OF PREFERRED EMBODIMENTS

Definitions

Figure 1:
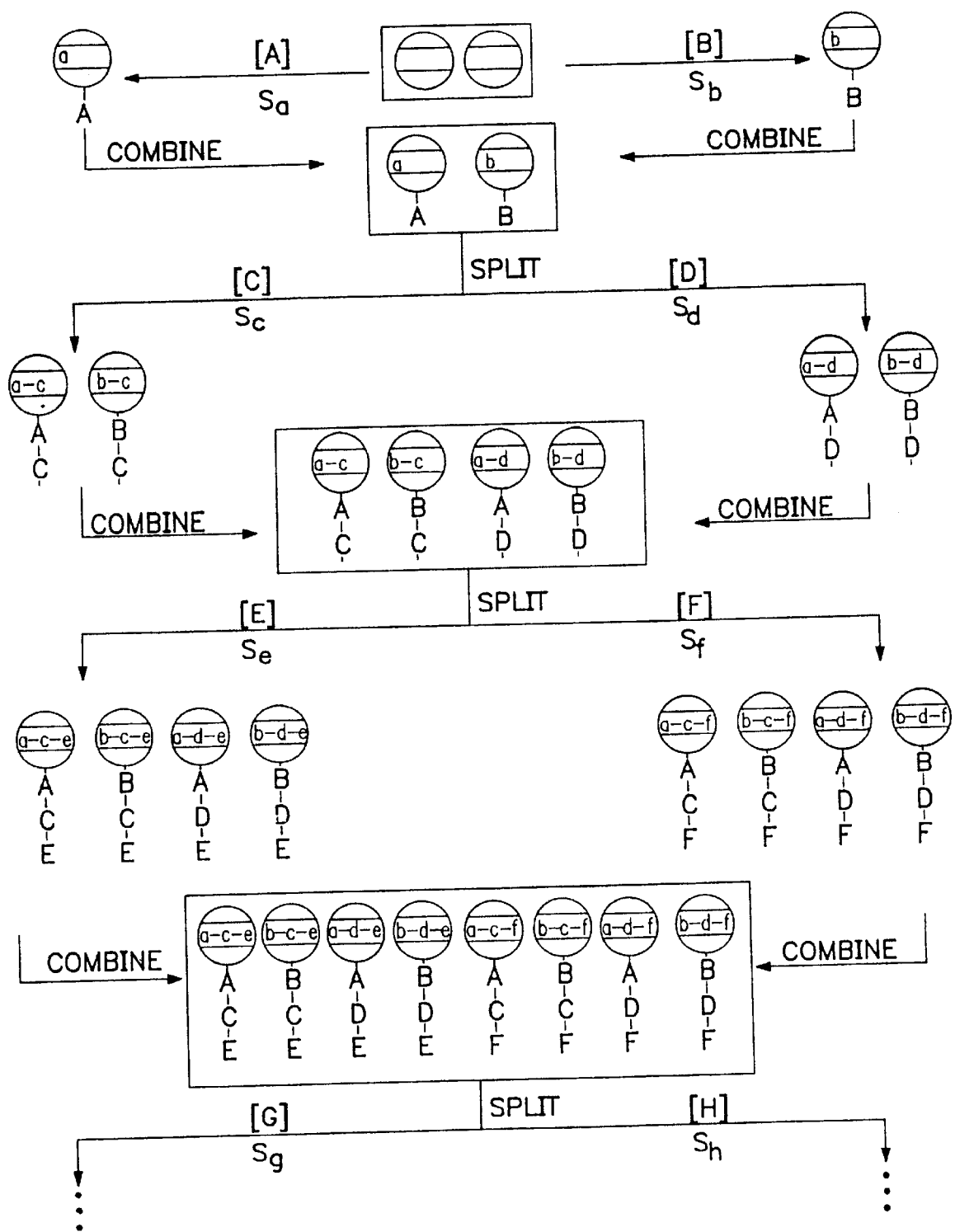
FIG. 1 depicts combinatorial synthesis of chemical libraries on matrix supports with memories. A, B, C . . . represent the chemical building blocks; a, b, c . . . represent the codes stored in memory that correspond to each of A, B, C, . . . , respectively.

Unless defined otherwise, all technical and scientific terms used herein have the same meaning as is commonly understood by one of skill in the art to which this invention belongs. All patents and publications referred to herein are, unless noted otherwise, incorporated by reference in their entirety.

As used herein, a matrix refers to any solid or semisolid or insoluble support to which the memory device and/or the molecule of interest, typically a biological molecule, organic molecule or biospecific ligand is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein may be particulate or may be a be in the form of a continuous surface, such as a microtiter dish or well, a glass slide, a silicon chip, a nitrocellulose sheet, nylon mesh, or other such materials. When particulate, typically the particles have at least one dimension in the 5–10 mm range or smaller. Such particles, referred collectively herein as "beads", are often, but not necessarily, spherical. Such reference, however, does not constrain the geometry of the matrix, which may be any shape, including random shapes, needles, fibers, elongated, etc. Roughly spherical "beads" are presently preferred. The "beads" may include additional components, such as magnetic or paramagnetic particles [see, e.g., Dyna beads (Dynal, Oslo, Norway)] for separation using magnets, as long as the additional components do not interfere with data entry or retrieval from the memory.

As used herein, matrix particles refer to matrix materials that are in the form of discrete particles. The particles have any shape and dimensions, but typically have at least one dimension that is 100 mm or less, preferably 50 mm or less, more preferably 10 mm or less, and typically have a size that is 100 $mm^3$ or less, preferably 50 $mm^3$ or less, more preferably 10 $mm^3$ or less, and most preferably 1 $mm^3$ or less. The matrices may also be continuous surfaces, such as microtiter plates [e.g., plates made from polystyrene or polycarbonate or derivatives thereof commercially available from Perkin Elmer Cetus, and Covalink trays [Nunc], microtiter plate lids or a test tube, such as a 1 ml eppendorf tube.

Matrices that are in the form of containers refers to containers, such as test tubes and microtiter plates and vials that are typically used for solid phase syntheses of combinatorial libraries or as vessels for screening and diagnostic assays. Thus, a container used for chemical syntheses refers to a container that typically has a volume of about 1 liter, generally 100 ml, and more often 10 ml or less, 5 ml or less, preferably 1 ml or less, and as small as about 50 $\mu l$–500 $\mu l$, such as 100 or 250 $\mu l$. This also refers to multi-well plates, such as microtiter plates. For example, the microtiter plate will typically contain a recording device in, on, or otherwise in contact with each of a plurality of wells.

As used herein, a matrix with a memory refers to a combination of a matrix with a miniature recording device that stores multiple bits of data by which the matrix may be identified, preferably in a non-volatile memory that can be written to and read from by transmission of electromagnetic radiation from a remote host, such as a computer. By miniature is meant of a size less than about 10 $mm^3$.

As used herein, a memory is a data storage unit [or medium] with programmable memory, preferably a non-volatile memory.

As used herein, programming refers to the process by which data or information is entered and stored in a memory. A memory that is programmed is a memory that contains retrievable information.

As used herein, remotely programmable/means that the memory can be programmed without direct physical or electrical contact or can be programmed from a distance, typically at least about 10 mm.

As used herein, a recording device is an apparatus that includes the data storage unit with programmable memory, and, if necessary, means for receiving information and for transmitting information that has been recorded. It includes any means needed or used for writing to and reading from the memory. The recording devices intended for use herein, are miniature devices that preferably are smaller than 10 $mm^3$, and more preferably are closer in size to 1 $mm^3$ or smaller that contain at least one such memory and means for receiving and transmitting data to and from the memory.

As used herein, a data storage unit with programmable memory includes any data storage means having the ability to record multiple discrete bits of data, which discrete bits of data may be individually accessed [read] after one or more recording operations. Thus, a matrix with memory is a combination of a matrix material with a miniature data storage unit.

As used herein, programmable means capable of storing unique data points. Addressable means having unique locations that may be selected for storing the unique data points.

As used herein, a host computer or decoder/encoder instrument is an instrument that has been programmed with or includes information [i.e., a key] specifying the code used to encode the memory devices. This instrument or one linked thereto transmits the information and signals to the recording device and it, or another instrument, receives the information transmitted from the recording device upon receipt of the appropriate signal. This instrument thus creates the appropriate signal to transmit to the recording device and can interpret transmitted signals. For example, if a "1" is stored at position 1, 1 in the memory of the recording device means, upon receipt of this information, this instrument or computer can determine that this means the linked molecule is, for example, a peptide containing alanine at the N-terminus, an organic group, organic molecule, oligonucleotide, or whatever this information has been predetermined to mean. Alternatively, the information sent to and transmitted from the recording device can be encoded into the appropriate form by a person.

As used herein, an electromagnetic tag is a recording device that has a memory that contains unique data points that correspond to information that identifies molecules or biological particles linked to, directly or indirectly, in physical contact with or in proximity to the device. Thus, electromagnetic tagging is the process by which identifying or tracking information is transmitted to the recording device.

As used herein, proximity means within a very short distance, generally less than 0.5 inch, typically less than 0.2 inches. In particular, stating that the matrix material and memory, or the biological particle or molecule and matrix with memory are in proximity means that, they are at least or at least were in the same reaction vessel or, if the memory is removed from the reaction vessel, the identity of the vessel containing the molecules or biological particles with which the memory was proximate or linked is tracked or otherwise known.

As used herein, antifuse refers to an electrical device that is initially an open circuit that becomes a closed circuit during programming, thereby providing for non-volatile memory means and permitting remote programming and, hence identification. In practice, an antifuse is a substantially nonconductive structure that is capable of becoming substantially conductive upon application of a predetermined voltage, which exceeds a threshold voltage. An antifuse memory does not require a constant voltage source for refreshing the memory and, therefore, may be incorporated in a passive device.

As used herein, passive device refers to an electrical device which does not have its own voltage source and relies upon a transmitted signal to provide voltage for operation.

As used herein, electromagnetic [EM] radiation refers to radiation understood by skilled artisans to be EM radiation and includes, but is not limited to radiofrequency [RF], infrared [IR], visible, ultraviolet [UV] radiation, X-rays, and laser light, coherent or otherwise.

As used herein, information identifying or tracking a biological particle or molecule, refers to any information that identifies the molecule or biological particle, such as, but not limited to the identity of the particle [i.e. its chemical formula or name], its sequence, its type, its class, its purity, its properties, such as its binding affinity for a particular ligand. Tracking means the ability to follow a molecule or biological particle through synthesis and/or process steps.

The memory devices herein store unique indicators that represent any of this information.

As used herein, combinatorial chemistry is a synthetic strategy that produces large chemical libraries. It is the systematic and repetitive, covalent connection of a set, the basis set, of different monomeric building blocks of varying structure to each other to produce an array of diverse molecules [see, e.g., Gallop et al. (1994) *J. Medicinal Chemistry* 37:1233–1251].

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, and other such biological materials.

As used herein, the molecules in the combinations include any molecule, including nucleic acids, amino acids, other biopolymers, and other organic molecules, including peptidomimetics and monomers or polymers of small organic molecular constituents of non-peptidic libraries, that may be identified by the methods here.

As used herein, the term "bio-oligomer" refers to a biopolymer of less than about 100 subunits. A bio-oligomer includes, but is not limited to, a peptide, i.e., containing amino acid subunits, an oligonucleotide, i.e., containing nucleotide subunits, a peptide-oligonucleotide chimera, and a peptidomimetic.

As used herein, the term "sequences of random monomer subunits" refers to polymers or oligomers containing sequences of monomers in which any monomer subunit may proceed or follow any other monomer subunit.

As used herein, the term "library" refers to a collection of substantially random compounds or biological particles expressing random peptides or proteins. Of particular interest are bio-oligomers, biopolymers, or diverse organic compounds or a set of compounds prepared from monomers based on a selected pharmacophore.

As used herein, an analyte is any substance that is analyzed or assayed in the reaction of interest. Thus, analytes include the substrates, products and intermediates in the reaction, as well as the enzymes and cofactors.

As used herein, multianalyte analysis is the ability to measure many analytes in a single specimen or to perform multiple tests from a single specimen. The methods and combinations herein provide means to identify or track individual analytes from among a mixture of such analytes.

As used herein, a peptidomimetic is a compound that mimics the conformation and certain stereochemical features of the biologically active form of a particular peptide. In general, peptidomimetics are designed to mimic certain desirable properties of a compound but not the undesirable features, such as flexibility leading to a loss of the biologically active conformation and bond breakdown. For example, methylenethio bioisostere [$CH_2S$] has been used as an amide replacement in enkephalin analogs [see, e.g., Spatola, A. F. *Chemistry and Biochemistry of Amino Acids, Peptides, and Proteins* [Weinstein, B, Ed., Vol. 7, pp. 267–357, Marcel Dekker, New York (1983); and Szelke et al. (1983) *In Peptides: Structure and Function, Proceedings of the Eighth American Peptide Symposium*, Hruby and Rich, Eds., pp. 579–582, Pierce Chemical Co., Rockford, Ill.].

As used herein, complete coupling means that the coupling reaction is driven substantially to completion despite or regardless of the differences in the coupling rates of individual components of the reaction, such as amino acids. In addition, the amino acids, or whatever is being coupled, are coupled to substantially all available coupling sites on the solid phase support so that each solid phase support will contain essentially only one species of peptide. Complete coupling will result in solid phase support/first amino acid combinations.

As used herein, the biological activity or bioactivity of a particular compound includes any activity induced, potentiated or influenced by the compound in vivo or in vitro. It also includes the abilities, such as the ability of certain molecules to bind to particular receptors and to induce a functional response. It may be assessed by in vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, substantially pure means sufficiently homogeneous to appear free of readily detectable impurities as determined by standard methods of analysis, such as thin layer chromatography [TLC], mass spectrometry [MS], size exclusion chromatography, gel electrophoresis, particularly agarose and polyacrylamide gel electrophoresis [PAGE] and high performance liquid chromatography [HPLC], used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound [see, e.g., Nogrady (1985) *Medicinal Chemistry A Biochemical Approach*, Oxford University Press, New York, pages 388–392].

As used herein, amino acids refer to the naturally-occurring amino acids and any other non-naturally occurring amino acids, and also the corresponding D-isomers. It is also understood that certain amino acids may be replaced by substantially equivalent non-naturally occurring variants thereof, such as D-Nva, D-Nle, D-Alle, and others listed with the abbreviations below or known to those of skill in this art.

As used herein, hydrophobic amino acids include Ala, Val, Leu, lle, Pro, Phe, Trp, and Met, the non-naturrally occurring amino acids and the corresponding D isomers of the hydrophobic amino acids, that have similar hydrophobic properties; the polar amino acids include Gly, Ser, Thr, Cys, Tyr, Asn, Gin, the non-naturrally occurring amino acids and the corresponding D isomers of the polar amino acids, that have similar properties, the charged amino acids include Asp, Glu, Lys, Arg, His, the non-naturrally occurring amino acids and the corresponding D isomers of these amino acids.

As used herein, Southern, Northern, Western and dot blot procedures in which DNA, RNA and protein patterns, respectively, are transferred from agarose gels to nitrocellulose membranes for hybridization or antibody or antigen binding are well known to those of skill in this art [see, e.g., Southern (1975) *J. Mol. Biol.* 98:503–517; Ketner et al. (1976) *Proc. Natl. Acad. Sci. U.S.A.* 73:1102–1106; Towbin et al. (1979) *Proc. Natl. Acad. Sci. U.S.A.* 76:4350].

As used herein, the abbreviations for amino acids and protective groups are in accord with their common usage and the IUPAC-IUB Commission on Biochemical Nomenclature [see, (1972) *Biochem.* 11: 1726]. Each naturally occurring L-amino acid is identified by the standard three letter code or the standard three letter code with or without the prefix "L-"; the prefix "D-" indicates that the stereoisomeric form of the amino acid is D. For example, as used herein, BOP is benzotriazol-1-yloxytris(dimethylamino) phosphonium hexafluorophosphate, DCC is dicyclohexylcarbodiimide; DDZ is dimethoxydimethylbenzyloxycarbonyl; DMT is dimethoxytrityl; FMOC is fluorenylmethyloxycarbonyl; HBTU is 2-(1H-benzotriazol-1-yl)-1,1,3,3-tetramethyluronium/hexafluorophosphate; NV is nitroveratryl; NVOC is 6-nitroveratryloxycarbonyl and other photoremovable groups; DMF for N,N-dimethylformamide; Boc is tert-butoxycarbonyl; TFA for trifluoroacetic acid; HF for hydrogen fluoride; HFIP for hexafluoroisopropanol; HPLC for high performance liquid chromatography; FAB-MS for fast atom bombardment mass spectrometry; DCM is dichloromethane, Bom is benzyloxymethyl; Pd/C is palladium catalyst on activated charcoal; DIC is diisopropylcarbodiimide; and [For] is formyl. Protected amino acids are readily available to those of skill in this art. For example, Fmoc and Boc protected amino acids can be obtained from Fluka, Bachem, Advanced Chemtech, Sigma, Cambridge Research Biochemical, Bachem, or Peninsula Labs or other chemical companies familiar to those who practice this art.

A. Matrices

Matrices, which are generally insoluble materials used to immobilize ligands and other molecules, have application in many chemical syntheses and separations. Matrices are used in affinity chromatography, in the immobilization of biologically active materials, and during chemical syntheses of biomolecules, including proteins, amino acids and other organic molecules and polymers. The preparation of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

Matrices include any material that can act as a support matrix for attachment of the molecules or biological particles of interest and can be in contact with or proximity to with, preferably encasing or coating, the data storage device with programmable memory. Any matrix composed of material that is compatible with and upon or in which chemical syntheses are performed, including biocompatible polymers, is suitable for use herein. The matrix material should be selected so that it does not interfere with the chemistry or biological reaction of interest [see, e.g., U.S. Pat. No. 4,006,403]. These matrices, thus include any material to which the data storage device with memory can be attached, placed in proximity thereof, impregnated, encased or otherwise connected, linked or physically contacted. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene crosslinked with divinylbenzene or the like [see, Merrifield (1964) *Biochemistry* 3:1385–1390], polyacrylamides, latex gels, polystyrene, dextran, polyacrylamides, rubber, silicon, plastics, nitrocellulose, celluloses, natural sponges, and many others. Among the preferred matrices are polymeric beads, such as the TentaGel™ resins and derivatives thereof [sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66; see, also Piskin et al. (1994), Chapter 18 "Nondegradable and Biodegradable Polymeric Particles" in *Diagnostic Biosensor Polymers,* ACS Symp. Series 556, Usmani et al. Eds, American Chemical Society, Washington, D.C.], which are designed for solid phase chemistry and for affinity separations and purifications.

Each such "bead" may contain one or more memories. In addition, the solid phase chemistry and subsequent assaying may be performed on the same bead. All procedures can be automated.

The matrices are typically insoluble substrates that are solid, porous, deformable, or hard, and have any required structure and geometry, including, but not limited to: beads, pellets, disks, capillaries, hollow fibers, needles, solid fibers, random shapes, thin films and membranes. Typically, when the matrix is particulate, the particles are at least about 10–2000 $\mu$m. For purposes herein, the support material will encase or be in contact with the data storage device, and, thus, will desirably have at least one dimension on the order of 1 mm [1000 $\mu$m] or more, although smaller particles may be contacted with the data storage devices. Each memory will be in contact with or proximity to at least one matrix particle, and may be in contact with more than one. As smaller semiconductor and electronic or optical devices become available, the size of the memory and size of the particles can be decreased. For example, presently, 0.5 micron semiconductor devices are available. Integrated circuits 0.25-micron in size have been described and are being developed using a technology called the Complementary Metal Oxide-Semiconductor process (see, e.g., Investor's Business Daily May 30, 1995).

Also larger matrix particles, which advantageously provide ease of handling, may be used and may be in contact with or proximity to more than one memory (i.e., one particle may have a plurality of memories in proximity or linked to it; each memory may programmed with different data regarding the matrix particle, linked molecules, synthesis or assay protocol, etc.]. Thus, so-called macro-beads (Rapp Polymere, Tubingen, Germany), which have a diameter of 2 mm when swollen, or other matrices of such size, are also contemplated for use herein. Particles of such size can be readily manipulated and the memory can be readily impregnated in or on the bead. These beads (available from Rapp) are also advantageous because of their uniformity in size, which is useful when automating the processes for electronically tagging and assaying the beads.

Selection of these matrices will be governed, at least in part, by their physical and chemical properties, such as solubility, functional groups, mechanical stability, surface area swelling propensity, hydrophobic or hydrophilic properties and intended use.

The data storage device with programmable memory may be coated with a material, such as a glass or a plastic, that can be further derivatized and used as the support or it may be encased, partially or completely, in the matrix material, such as during or prior to polymerization of the material. Such coating may be performed manually or may be automated. The coating can be effected manually or using instruments designed for coating such devices. Instruments for this purpose are available [see, e.g., the Series C3000 systems for dipping available from Specialty Coating Systems, Inc., Indianapolis, Ind.; and the Series CM 2000 systems for spray coating available from Integrated Technologies, Inc., Acushnet, Mass.].

The data storage device with memory may be physically inserted into the matrix material or particle. It also can be manufactured with a coating that is suitable for use as a matrix or that includes regions in the coating that are suitable for use as a matrix. If the matrix material is a porous membrane, it may be placed inside the membrane. It is understood that when the memory device is encased in the matrix or coated with protective material, such matrix or material must be transparent to the signal used to program the memory for writing or reading data. More than one matrix particle may be linked to each data storage device.

In some instances, the data storage device with memory is coated with a polymer, which is then treated to contain an appropriate reactive moiety or in some cases the device may be obtained commercially already containing the reactive moiety, and may thereby serve as the matrix support upon which molecules or biological particles are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethoxysilyl)propyl]phthelamic acid; and bis(2-hydroxyethyl)aminopropyltriethoxysilane. Exemplary of readily available materials containing amino group reactive functionalities, include, but are not limited to, para-aminophenyltriethoxysilane. Also derivatized polystyrenes and other such polymers are well known and readily available to those of skill in this art [the Tentagel® Resins] are available with a multitude of functional groups [sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66].

The data storage device with memory, however, generally should not or cannot be exposed to the reaction solution, and, thus, must be coated with at least a thin layer of a glass or ceramic or other protective coating that does not interfere with the operation of the device. These operations include electrical conduction across the device and transmission of remotely transmitted electromagnetic radiation by which data are written and read. It is such coating that may also serve as a matrix upon which the molecules or biological particles may be linked.

The data storage devices with memory may be coated either directly or following coating with a ceramic, glass or other material, may then be coated with agarose, which is heated, the devices are dipped into the agarose, and then cooled to about room temperature. The glass or silica or other coated semi-conductor devices, may be used as the matrix supports.

Conventional integrated circuit manufacturing and packaging methods include methods and means for encapsulating integrated circuits to protect the devices from the environment and to facilitate connection to external devices. Also, there are also numerous descriptions for the preparation of semiconductor devices and wires, particularly for use as biosensors [see, e.g., U.S. Pat. No. 4,933,285; see, also Cass, Ed. (1990) *Biosensors A Practical Approach,* IRL Press at Oxford University Press, Oxford; (biosensors are chemosensors with a biological detection system, generally biologically active substances, such as enzymes, antibodies, lectins and hormone receptors, which are immobilized on the surface of the sensor electrode or in a thin layer on the sensor electrode], which measure electrochemical solution parameters, such as pH. Despite differences in the components of biosensors and recording devices used herein, which include memories, are remotely programmable and identify or track linked or proximate molecules and biological particles and do not measure the electrochemistry of the solution, certain of the methods for coating electrodes and wires in the biosensor art may be adapted for use herein [see, e.g., U.S. Pat. Nos. 5,342,772, 5,389,534, 5,384,028, 5,296,122, 5,334,880, 5,311,039, 4,777,019, 5,143,854, 5,200,051, 5,212,050, 5,310,686, 5324,591; see, also Usmani et al., ed. (1994) *Diagnostic Biosensor Polymers,* ACS Symposium Series No. 556].

It is, however, emphasized that the combinations herein are not biosensors, which include electrodes that must be in contact with the solution such that molecules in solution directly contact the electrode, and which measure solution parameters. The combinations herein are matrix materials with recording devices that contain data storage units that include remotely programmable memories; the recording devices used in solution must be coated with a material that prevents contact between the recording device and the solution.

1. Natural Matrix Support Materials

Naturally-occurring supports include, but are not limited to agarose, other polysaccharides, collagen, celluloses and derivatives thereof, glass, silica, and alumina. Methods for isolation, modification and treatment to render them suitable for use as supports is well known to those of skill in this art [see, e.g., Hermanson et al. (1992) *Immobilized Affinity Ligand Techniques,* Academic Press, Inc., San Diego]. Gels, such as agarose, can be readily adapted for use herein. Natural polymers such as polypeptides, proteins and carbohydrates; metalloids, such as silicon and germanium, that have semiconductive properties, as long as they do not interfere with operation of the data storage device may also be adapted for use herein. Also, metals such as platinum, gold, nickel, copper, zinc, tin, palladium, silver, again as long as the combination of the data storage device with memory, matrix support with molecule or biological particle does not interfere with operation of the device with memory, may be adapted for use herein. Other matrices of interest include oxides of the metal and metalloids such as Pt—PtO, Si—SiO, Au—AuO, TiO2, Cu—CuO, and the like. Also compound semiconductors, such as lithium niobate, gallium arsenide and indium-phosphide, may be used as matrices. Methods for preparation of such matrix materials are well known.

For example, U.S. Pat. No. 4,175,183 describes a water insoluble hydroxyalkylated cross-linked regenerated cellulose and a method for its preparation. A method of preparing the product using near stoichiometric proportions of reagents is described. Use of the product directly in gel chromatography and as an intermediate in the preparation of ion exchangers is also described.

2. Synthetic Matrices

There are innumerable synthetic matrices and methods for their preparation known to those of skill in this art. Synthetic matrices are typically produced by polymerization of functional matrices, or copolymerization from two or more monomers of from a synthetic monomer and naturally occurring matrix monomer or polymer, such as agarose. Before such polymers solidify, they are contacted with the data storage device with memory, which can be cast into the material or dipped into the material. Alternatively, after preparation of particles or larger synthetic matrices, the recording device containing the data storage unit(s) can be manually inserted into the matrix material. Again, such devices can be pre-coated with glass, ceramic, silica or other suitable material.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers [see, e.g., Merrifield (1964) *Biochemistry* 3:1385–1390; Berg et al. (1990) in *Innovation Perspect. Solid Phase Synth. Collect. Pap.,* Int. Symp., 1st, Epton, Roger (Ed), pp. 453–459; Berg et al. (1989) in *Pept., Proc. Eur. Pept. Symp.,* 20th, Jung, G. et al. (Eds), pp. 196–198; Berg et al. (1989) *J. Am. Chem. Soc.* 111: 8024–8026; Kent et al. (1979) *Isr. J. Chem.* 17:243–247; Kent et al. (1978) *J. Org. Chem.* 43:2845–2852; Mitchell et al. (1976) *Tetrahedron Lett.* 42:3795–3798; U.S. Pat. No. 4,507,230; U.S. Pat. No. 4,006,117; and U.S. Pat. No. 5,389,449]. Methods for preparation of such matrices are well-known to those of skill in this art.

Synthetic matrices include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes have also been used as solid supports for affinity purifications [Powell et al. (1989) *Biotechnol. Bioeng.* 33:173].

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly (propyleneoxy) glycol or a poly(butyleneoxy) glycol. In producing these polymers, an organic polyamine is used as a crosslinking agent. Other matrices and preparation thereof are described in U.S. Pat. Nos. 4,177,038, 4,175,183, 4,439, 585, 4,485,227, 4,569,981, 5,092,992, 5,334,640, 5,328,603

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halomethyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

3. Immobilization and Activation

Numerous methods have been developed for the immobilization of proteins and other biomolecules onto solid or liquid supports [see, e.g., Mosbach (1976) *Methods in Enzymology* 44; Weetall (1975) *Immobilized Enzymes, Antigens, Antibodies, and Peptides;* and Kennedy et al. (1983) *Solid Phase Biochemistry, Analytical and Synthetic Aspects,* Scouten, ed., pp. 253–391]. The most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, e.g., the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking,* CRC Press]. To effect immobilization, a solution of the protein or other biomolecule is contacted with a support material such as alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840].

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal [see, e.g., U.S. Pat. No. 4,179,402; and Smith et al. (1992) *Methods: A Companion to Methods in Enz.* 4:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885,250]. In this method the biomolecule is first modified by reaction with a perfluoroalkylating agent such as perfluorooctylpropylisocyanate described in U.S. Pat. No. 4,954,444. Then, the modified protein is adsorbed onto the fluorocarbon support to effect immobilization.

The activation and use of matrices are well known and may be effected by any such known methods [see, e.g., Hermanson et al. (1992) *Immobilized Affinity Ligand Techniques,* Academic Press, Inc., San Diego]. For example, the coupling of the amino acids may be accomplished by techniques familiar to those in the art and provided, for example, in Stewart and Young, 1984, *Solid Phase Synthesis,* Second Edition, Pierce Chemical Co., Rockford.

B. Data Storage Units with Memory

Any remotely programmable data storage device that can be linked to or used in proximity to the solid supports and molecules and biological particles as described herein is intended for use herein. Preferred devices are rapidly and readily programmable using penetrating electromagnetic radiation, such as radio frequency or visible light lasers, operate with relatively low power, have fast access [$10^{-3}$ sec], and are remotely programmable so that information can be stored or programmed and later retrieved from a distance, as permitted by the form of the electromagnetic signal used for transmission. A transmitter/receiver system, which is preferably integrated on the same substrate as the memory, supplies the power to program and retrieve the data stored in the chip memory.

This remotely programmable device can be programmed sequentially to be uniquely identifiable during and after stepwise synthesis of macromolecules or before or after selection of screened molecules. In certain embodiments herein, the data storage units are information carriers in which the functions of writing data and reading the recorded data are empowered by an electromagnetic signal generated and modulated by a remote host controller. Thus, the data storage devices are inactive, except when exposed to the appropriate electromagnetic signal. In an alternative embodiment, the devices may be optically or magnetically programmable read/write devices.

Electromagnetically Programmable Devices

The programmable devices intended for use herein, include any device that can record or store data. The preferred device will be remotely programmable and will be small, typically on the order of 1 mm$^3$ or smaller. Any means for remote programming and data storage, including semiconductors and optical storage media are intended for use herein.

In a preferred embodiment herein, the data storage unit includes a semiconductor chip with integrated circuits formed thereon including a memory and its supporting circuitry. These devices can be written to and interrogated from a distance. A radiofrequency transmitter/receiver system supplies power to the chip to program and retrieve data. In particular, the data storage unit preferably includes a programmable read only semiconductor memory [PROM], preferably a non-volatile memory, which will have information describing or identifying the molecules or biological particles linked to or in proximity to the matrix. This information either identifies the molecule or biological particles including a phage and viral particles, bacteria, cells and fragments thereof, provides a history of the synthesis of the molecule, or provides information, such as a batch number or identity of the linked entity. The memory is programmed, before, during or, preferably, after, each step of synthesis and can thereafter be read, thereby identifying the molecule or its components and order of addition, or process of synthesis.

While many well known read only memory devices utilize fuse structures that are selectively "blown" to store data points, with a fuse located at each possible data address in an array, the devices of particular interest herein rely on antifuse programming technology, in which short circuits are selectively created through an insulating layer separating word and bit lines in an array. Antifuse memories are preferred due to the lower voltage requirements for writing. The memory devices, which are about 1 mm$^3$ in size or less, are rapidly programmable [1 sec, preferably 1 msec or less], can be interrogated from a distance, and are programmable using electromagnetic radiation, preferably of a frequency, such as radiofrequencies, that do not alter the assessed activities of the molecules and biological particles of interest. Devices that rely on other programmable memories are also intended for use herein.

Antifuses

An antifuse contains a layer of antifuse material sandwiched between two conductive electrodes. The antifuse device is initially an open circuited device in its unprogrammed state and can be irreversibly converted into an essentially short circuited device by the application of a programming voltage across the two electrodes to disrupt the antifuse material and create a low resistance current path between the two electrodes.

An exemplary antifuse structure for use herein is formed by defining a word line of heavily N-doped polysilicon on an insulating substrate, depositing an antifuse layer of lightly N-doped semiconductor over the polysilicon, and defining a metal address [or bit] line upon and in electrical contact with the antifuse layer. The semiconductor material used for the antifuse layer is typically selected from among silicon, germanium, carbon and alpha-tin. The properties of the semiconductor material are such that the material is essentially non-conductive as long as the voltage across it does not exceed a threshold level. Once the threshold voltage is exceeded, a conductive filament is formed through the semiconductor so that the resistance between the metal and polysilicon lines at the points at which they cross irreversibly switches from a high resistance state to a relatively low resistance state.

To program or change the resistance of the antifuse from a very high level [greater than 100,000,000 ohms] to a low level [less than 1000 ohms], a voltage of sufficiently high electrical field strength is placed across the antifuse film to create a short circuit. The voltage level required to induce breakdown is determined by the level of dopant in the antifuse layer. As breakdown occurs electrical current will flow through one small region of the film. The current is limited by the resistance of the filament itself as well as any series resistance of conductive layers or logic devices [transistors] in series with the antifuse.

Examples of the antifuse and its use as a memory cell within a Read-Only Memory are discussed in Roesner, "Method of Fabricating a High Density Programmable Read-Only Memory", U.S. Pat. No. 4,796,074 (1989) and Roesner, "Electrically Programmable Read-Only Memory Stacked above a Semiconductor Substrate", U.S. Pat. No. 4,442,507 (1984). A preferred antifuse is described in U.S. Pat. No. 5,095,362. "Method for reducing resistance for programmed antifuse" (1992). U.S. Pat. No. 5,095,362 provides a method for fabricating a layer of programmable material within an antifuse that exhibits relatively lower than normal resistance in its programmed state and also provides a semiconductor device containing an antifuse film of the type composed of semiconductor material having a first electrical state that is characterized by high electrical resistivity and a second electrical state that is characterized by low electrical resistivity.

The means for selectively decreasing resistivity includes nonactivated conductive dopants that are ion implanted within the otherwise highly resistive semiconductor material. The dopants as implanted are in a nonactivated state so that the dopants do not enhance the conduction of carriers in the film. Once activated, the dopants enhance the conduction of carriers in the film. Activation of the dopants occurs upon application of a threshold voltage across a predetermined and selected portion of the material in which the dopants are disposed. The selected portion is defined by the crossover point of selected word and bit [or address] lines. The dopants are N-type, selected from among antimony, phosphorous, arsenic, and others to provide additional charge carriers. The implant dosage is used to determine the threshold voltage level that will be required to induce formation of the conductive filament. P-type dopants, such as boron, may also be used to affect a change in programming voltage.

A Preferred Recording Device with Non-volatile, Anti-fuse-based Memory

Figure 5:
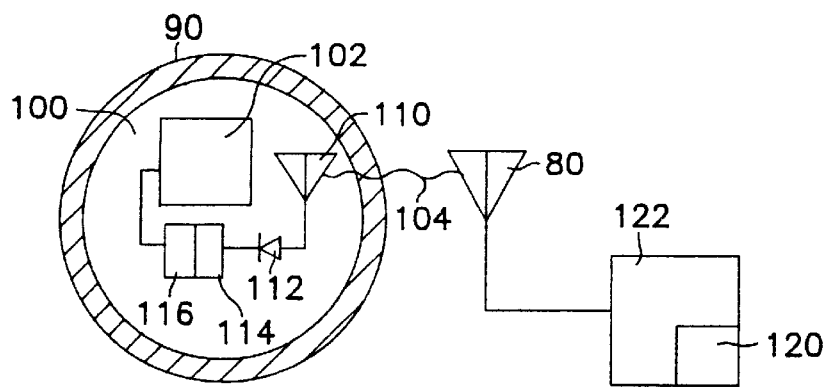
FIG. 5 is a block diagram of the data storage means and supporting electrical components of a preferred embodiment.

Referring to FIG. 5, which depicts a preferred embodiment, a recording device containing a non-volatile electrically-programmable read-only memory [ROM] 102 that utilizes antifuse technology is combined on a single substrate 100 with a thin-film planar antenna 110 for receiving/transmitting an RF signal 104, a rectifier 112 for deriving a voltage from a received radio frequency [RF] signal, an analog-to-digital converter [ADC] 114 for converting the voltage into a digital signal for storage of data in the memory, and a digital-to-analog converter [DAC] 116 for converting the digital data into a voltage signal for transmission back to the host computer is provided. A single substrate 100 is preferred to provide the smallest possible chip, and to facilitate encapsulation of the chip with a protective, polymer shell [or shell+matrix or matrix material] 90. Shell 90 must be non-reactive with and impervious to the various processes that the recording device is being used to track in order to assure the integrity of the memory device components on the chip. Materials for the shell include any such materials that are known to those of skill in the art [see, e.g., Hiroshi et al., eds. (1995) *Polymeric Materials for Microelectronic Applications: Science and Technology*, ACS Symposium Series No. 579], including glasses, ceramics, plastics and other inert coatings.

Based on current semiconductor integrated circuit fabrication process capabilities, in a preferred embodiment the finished chip on which all of the listed components are integrated is on the order of 1 mm×1 mm [~40 mils×40 mils], with a memory capacity of 1024 bits. Greater memory capacity, where needed, and smaller chips, however, will be preferred. The chip may be larger to accommodate more memory if desired, or may be smaller as design rules permit smaller transistors and higher device densities, i.e., greater memory capacity.

The antifuse ROM structure described herein, and the method for fabricating the same, are based upon the teachings of U.S. Pat. No. 4,424,579, issued Jan. 3, 1984, U.S. Pat. No. 4,442,507, issued Apr. 10, 1984, U.S. Pat. No. 4,796,074, issued Jan. 3, 1989, and U.S. Pat. No. 5,095,362, issued Mar. 10, 1992, all of Roesner, U.S. Pat. No. 4,598,386, issued Jul. 1, 1986, of Roesner et al., and U.S. Pat. No. 5,148,256, issued Sep. 15, 1992 and U.S. Pat. No. 5,296,722, issued Mar. 22, 1994, both of Potash, et al., all of which are incorporated herein by reference.

In an antifuse-type memory device, the individual memory cells are arranged in matrices of orthogonal conductive word and bit lines to obtain the smallest possible memory array size. For example, for 1024 bits of memory, there are 32 word lines and 32 bit lines for a square matrix. Memories with greater capacity may also be used. Schottky diodes are formed generally corresponding to the points at which the word and bit lines cross. The word and bit lines are separated by an undoped or lightly-doped semiconductor layer with interstitial doping. The semiconductor layer may also be amorphous silicon with implanted dopants in a nonactivated state. Each of these crossover points is a memory cell and is the equivalent of a programmable switch in series with a Schottky diode. Data are stored by the switch being ON or OFF. As fabricated, an antifuse memory device has all of its switches in the OFF state. A switch is turned on by applying a voltage in excess of a pre-determined threshold voltage to one of the word lines while setting a selected bit line to a low logic level. The threshold voltage is determined by the impedance of the semiconductor layer, i.e., its doping level. According to the process for fabricating the antifuse memory of the preferred embodiment, the impedance can be less than 200 ohms with a threshold voltage for programming as low as 3 volts. Since in the embodiment described herein the programming voltage is provided solely by the rectified RF signal, a low threshold is preferred. Application of voltage exceeding the threshold activates the interstitial dopant in the semiconducting film at the point corresponding to the cross-over between the two lines, causing a short between the word and bit lines and irreversibly turning on that particular switch or memory cell. Address decoders, as are known in the art, are used to selectively address the word and bit lines for purposes of both writing information to and reading stored information from the memory array. Exemplary means for decoding information to be stored in memory and to be read from memory are provided in U.S. Pat. Nos. 4,442,507 and 4,598,386.

Information to be written into the memory need not be detailed since the data stored in the memory is primarily acting as an identification marker that is traceable to a more detailed record stored in the host computer memory 120, independent of the memory associated with the matrix support or tagged molecule or biological particle. In this manner, the RF signal from transmitter 80 that is used to provide the power and the signal to the matrix particle memory need only address a single memory cell to indicate that a nascent oligomer linked to or in proximity to the memory device has been subjected to a given process step or to identify a molecule or biological particle. In other words, a conventional "push-pull" type of address decoder, where only one bit line and one word line are driven high and low, respectively, at any given time, may be used. Thus, a sophisticated memory addressing system need not be provided on the matrix particle memory chip, and shift registers may be used to control memory addressing. Alternatively, a microprocessor which is mask-programmed during the fabrication process for controlling an address bus which connects the ADC 114 and the DAC 116 to the memory array may also be built onto the same substrate on which the memory and other components are integrated. Other integrated means for selectively addressing locations within the memory are known and will be apparent to the practitioner skilled in the art.

As described above, antifuse memories are well known in the art. These memories include structures in which the word and bit lines may both be made of either N+ polysilicon or metal [aluminum or aluminum-silicon], separated by silicon dioxide ($SiO_2$), silicon nitride ($Si_3N_4$), combinations thereof, or amorphous silicon alone or in combination with $SiO_2$ and/or $Si_3N_4$. In each case, a short circuit is created at locations in the antifuse material corresponding to the crossover location of selected word and bit lines by applying a voltage in excess of a pre-determined threshold voltage.

Examples of alternate means for forming an antifuse memory are provided in the following: U.S. Pat. No. 5,248,632, issued Sep. 28, 1993, of Tung et al.; U.S. Pat. No. 5,250,459, issued Oct. 5, 1993, of Lee, U.S. Pat. No. 5,282,158, issued Jan. 25, 1994, of Lee; U.S. Pat. No. 5,290,734, issued Mar. 1, 1994, of Boardman, et al.; U.S. Pat. No. 5,300,456, issued Apr. 5, 1994, of Tigelaar et al.; U.S. Pat. No. 5,311,039, issued May 10, 1994, of Kimura, et al.; U.S. Pat. No. 5,316,971, issued May 31, 1994, of Chiang et al.; U.S. Pat. No. 5,322,812, issued Jun. 21, 1994, of Dixit, et al.; U.S. Pat. No. 5,334,880, issued Aug. 2, 1994, of Abadeer, et al., and others. In addition to antifuse memory devices, other types of electrically-programmable read-only memories, preferably non-volatile memories, which are known in the art, may be used. Note that non-volatility of the memory is important since power is applied to the chip only when it is subjected to the RF or other transmission signal. Further considerations are the voltage levels required for writing into memory, since the threshold voltage must be less than the maximum voltage of the rectified RF signal in order to assure that sufficient voltage is always available during the writing process. The write voltage may be enhanced by supplementing the RF-supplied voltage with optically-generated voltage, such as a photocell. Photocells on semiconductor substrates are well known in the art and could be easily integrated onto the chip. A laser or other light source could be readily included in the write apparatus to illuminate the chip coincident with transmission of the RF write signal. Similarly, other forms of electromagnetic radiation may be used to provide additional power, if needed.

Although antifuse memories are not designed to be erasable, it may be desirable to re-use the devices if the memory becomes full. In such instances, conventional electrically programmable erasable read only memories [EEPROMs] may be used instead. Since EEPROMs require higher write voltage levels, it may be desirable to supplement the RF-supplied voltage as described above. In EEPROMs, stored data can be erased by exposing the device to UV light.

Signal rectifier 112 may be one or more Schottky diode(s), making it readily incorporated into the fabrication process used for the memory array. Other means for signal rectification may be used as are known. The ADC 114 and DAC 116 are well-known devices and are readily integrated onto the substrate 100 using the fabrication process described in the references for the memory array. Radio frequency modulation techniques, which are known in the art, for example, pulse code modulation, may be adapted to permit direct digital transmission, in which case the ADC and DAC may not be required.

Antenna 110 is formed during the fabrication process using conventional photolithographic techniques to provide one or more metal structures, such as aluminum, to receive a pre-determined wavelength RF transmission. The antenna may be a simple straight line half-wave antenna which is created by patterning a structure during the second metal process steps so that the structure has a length equal to one-half of the wavelength of the selected RF transmission frequency in free space. Another option for formation of the antenna is as a small loop, either on a dedicated portion of the chip, or encircling the other components of the chip, also formed during the second metal step of the fabrication process. It is noted that, in a typical semiconductor fabrication process, such as would be compatible with the preferred antifuse memory, the first and second metal steps include depositing a layer of aluminum, then patterning the aluminum photolithographically followed by a plasma etch to define the desired features. Except where vias are formed, the two metal layers are separated by a dielectric film. Dipole antennas may be formed by patterning the second metal in a similar manner, with the dimensions of the antenna being selected for the appropriate RF frequency. The two metal layers may also be used to form a microstrip antenna structure by selecting the dielectric film between the metal layers such that it has a dielectric constant and thickness appropriate so that the microstrip is resonant at one-half of the RF wavelength. [The first metal layer provides the ground plane.] The metal structures, which may be square patches, circles, lines, or other geometries, are defined photolithographically during the normal masking steps of the first and second metal processes. Other antenna structures which can be configured as a thin film device for integration onto a common substrate with the memory structure and other components may be used and will be apparent to those skilled in the art. Similarly, a resonant circuit [inductor-capacitor] can be readily integrated onto the chip, with the resonant circuit being tuned to the RF carrier signal of the transmitter.

Frequency tuning of either an antenna or resonant circuit can provide additional coding capability. For example, a first group of memory devices can be tuned to receive a carrier wave of a first RF frequency, e.g., $f_1$, and a second group could be tuned to receive a second frequency $f_2$, and so on. The separate carrier frequencies could provide additional means for keeping track of the devices, even if the groups become intermixed.

The RF antenna may, in an alternate embodiment, be formed external to the semiconductor substrate. In this configuration, a separate conductive wire, which acts as an antenna, will be attached to a bond pad formed on the chip using methods known to those skilled in the art. The wire will then be stabilized when the chip is encased in the protective shell, so that the antenna extends at some angle to the chip.

Also, as an alternative to signal transmission via RF, the antifuse or other semiconductor memory and supporting circuitry can receive the addressing commands and device power by optical transmission. In this embodiment, the RF antenna 110 would be replaced by a photocell that generates sufficient write voltage to exceed the threshold voltage. For the addressing commands, the RF transmitter 80 is replaced by a light source, and the commands may be transmitted digitally by pulsing the optical transmitter, which can be a laser, flash lamp or other high intensity light source. It is noted that the light intensity must be sufficient to generate adequate voltage in the photocell to write into memory, but not so high that it damages the metal interconnect on the chip. With digital data transmission analog-to-digital and digital-to-analog conversion circuitry can be eliminated.

Figure 6:
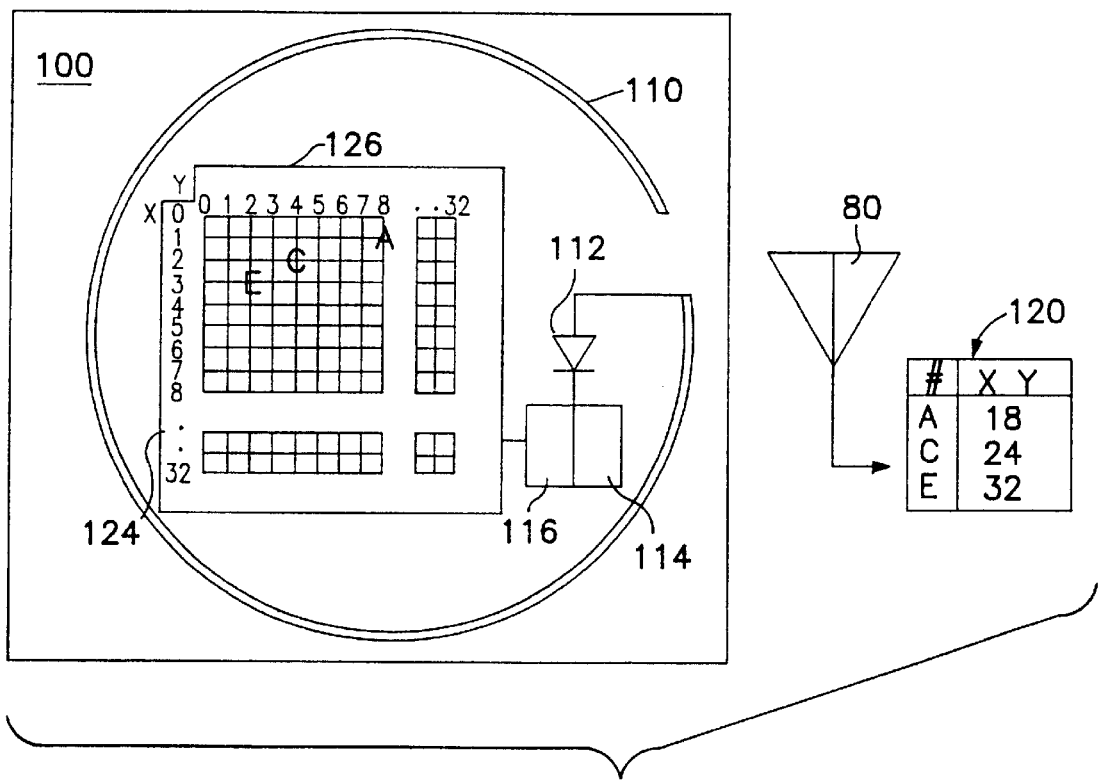
FIG. 6 is a diagrammatic view of the memory array within the recording device, and the corresponding data stored in the host computer memory.

The operation of programming the memory to record the process steps to which the linked or adjacent matrix particle or support and linked or proximate molecule or biological particle is exposed involves placing the memory device reasonably close [a distance on the order of about 1 inch [25.4 mm] is presently contemplated, but longer distances should be possible, and can be determined empirically] to RF transmitter 80. The RF transmitter 80 emits a carrier wave modulated by a signal generated by host computer 122 using conventional RF technology. The carrier wave itself can provide the power to the generate the programming voltage and the operating voltage for the various devices via the rectifier, while the modulation signal provides the address instructions. As stated previously, since the memory need only be tagged to record the exposure of the proximate or linked molecule or biological particle to a given process, the address signal need only carry information to turn on a single memory location, while the host computer 122 stores into memory 120 the information linking the process information with the single memory location that was "tagged" to record exposure to the process step. Referring to FIG. 1, in which chemical building blocks A, C, and E are added to a molecule linked to a matrix with memory, and to FIG. 6, an illustrative example of how information is written onto a particle is provided in Table 1.

TABLE 1

| PROCESS STEP | X-REGISTER ADDRESS | Y-REGISTER ADDRESS |
|---|---|---|
| A | 1 | 8 |
| C | 2 | 4 |
| E | 3 | 2 |

For the step in which A is added, the address signal would increment the x-register 124 one location and increment the y-register 126 eight locations, and then apply the programming voltage. The activation of this switch is indicated by an "A" at the selected address, although the actual value stored will be a binary "1", indicating ON. [As described, for example, in U.S. Pat. No. 4,424,579, how the programming voltage is applied depends on whether the decoders have depletion or enhancement transistors.] The host computer 122 would write into its memory 120 that for process A, the x-,y- address is 1,8. Upon removal of the RF signal after recording process A, the voltage is removed and the registers would reset to 0. For the step in which C is added, the address signal would increment the x-register 124 two locations and the y-register 126 four locations, then apply the programming voltage, as indicated by the letter "C". The host computer 120 would similarly record in memory that an indication of exposure to process C would be found at x-,y- address 2,4. Again, upon removal of the RF signal, the registers reset to 0 so that when the matrix particle's memory is again exposed to RF following addition of block E, the registers increment 3 and 2 locations, respectively, and the programming voltage is applied to turn on the switch, indicated by "E". Desirably all processing steps are automated.

After processing is completed, to read the information that has been recorded in the memory of the data storage unit, the host computer 122 will inquire into the identity of the particle by generating a command signal to the registers to select the appropriate address locations to determine whether the switch is on or off. If the switch is on, i.e., a voltage drop occurs at that point, the computer will create a record that the particle received a particular process step. Alternatively, the host computer can generate an inquiry signal to sequentially look at all memory locations to determine which switches have been turned on, recording all locations at which voltage drops occurred. The computer will then compare the "on" locations to the process steps stored in its memory to identify the steps through which the subject particle was processed.

If desired, individual particles can be identified by reserving certain memory locations for identification only, for example, the first two rows of the x-register. In this case, particles will be passed separately through the RF signal while the x-register is incremented to turn on switches at address locations 0,0, 1,0, 2,0, etc. With individual identification, the host computer 122 can first generate a signal to query a matrix particle memory to determine its identity, then write the information with regard to the process performed, saving the process and particle information in the host computer memory 120.

Ideally, the tagging of particles which are exposed to a particular process would be performed in the process vessel containing all of the particles. The presence, however, of a large number of particles may result in interference or result in an inability to generate a sufficiently high voltage for programming all of the particles simultaneously. This might be remedied by providing an exposure of prolonged duration, e.g., several minutes, while stirring the vessel contents to provide the greatest opportunity for all particles to receive exposure to the RF signal. On the other hand, since each particle will need to be read individually, a mechanism for separating the particles may be used in both write and read operations. Also, in instances in which each particle will have a different molecule attached, each particle memory must be addressed separately.

Figure 7:
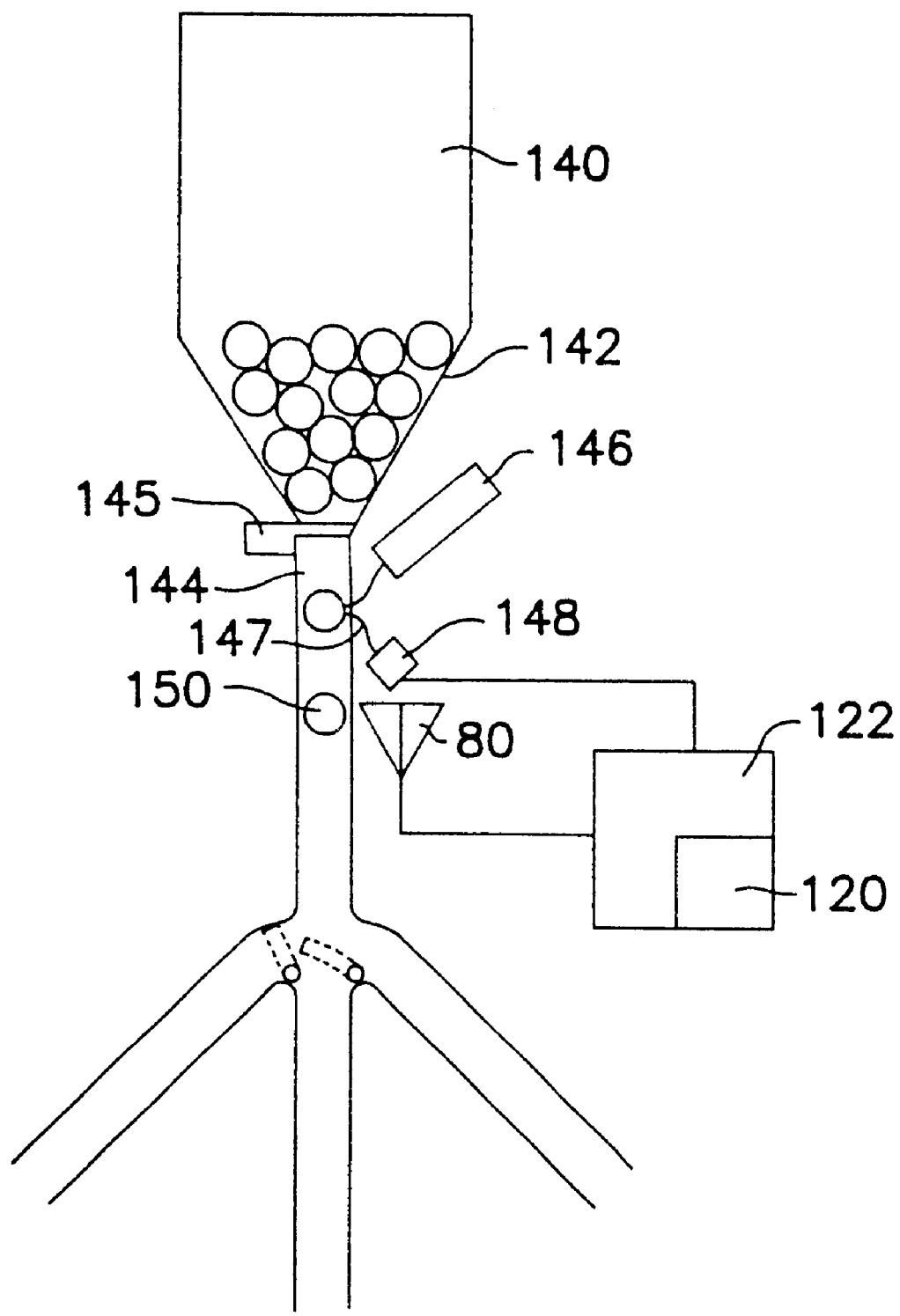
FIG. 7 is an illustration of an exemplary apparatus for separating the matrix particles with memories for individual exposure to an EM signal.

An apparatus for separating the particles to allow individual exposure to the RF signal is illustrated in FIG. 7. Here, the particles are placed in a vessel 140 which has a funnel 142, or other constricted section, which permits only one particle 150 to pass at a time. It is noted that the particles, as illustrated, are, for purposes of exemplification, depicted as spherical. The particles, however, can be of any shape, including asymmetric shapes. Where the particles are asymmetric or of other shapes, the size of the funnel exit and tube should be selected to fit the largest diameter of the particles closely. If a particular orientation of the particle is desired or required for effective transmission, the tube and funnel exit should be designed and oriented to permit only particles in the proper alignment with the tube to exit.

The RF transmitter 80 is positioned adjacent a tube 144 which receives input from funnel 142. When a particle passes through tube 144 the RF transmitter provides a signal to write to or read from the particle's memory. Means for initiating the RF transmission may include connection to a mechanical gate or shutter 145 in the funnel 142 which controls the admission of the particle into the tube. As illustrated in FIG. 7, however, optical means for detecting the presence of the matrix particle with memory to initiate RF transmission are provided in the form of a laser 146 directed toward the tube 144, which is transparent to the wavelength of the light emitted by the laser. When the laser light impinges upon the particle [shown with dashed lines] it is reflected toward an optical detector 148 which provides a signal to the host computer 122 to initiate the RF transmission. Alternatively, magnetic means, or any other means for detecting the presence of the particle in the tube 144 may be used, with the limitation that any electromagnetic radiation used does not induce any reactions in the substances on the particle's surface. After exposure of the individual particle to the RF signal, the particle may be received in one or more vessels for further processing. As illustrated, tube 144 has an exemplary three-way splitter and selection means, shown here in dashed lines as mechanical gates, for directing the particles to the desired destination.

Optically or Magnetically Programmed Devices

In addition to electrically-programmable means for storing information on the matrix particles, optical or magnetic means may be used. One example of an optical storage means is provided in U.S. Pat. No. 5,136,572, issued Aug. 4, 1992, of Bradley, which is incorporated herein by reference. Here, an array of stabilized diode lasers emits fixed wavelengths, each laser emitting light at a different wavelength. Alternatively, a tunable diode laser or a tunable dye laser, each of which is capable of emitting light across a relatively wide band of wavelengths, may be used. The recording medium is photochemically active so that exposure to laser light of the appropriate wavelength will form spectral holes.

Figure 8:
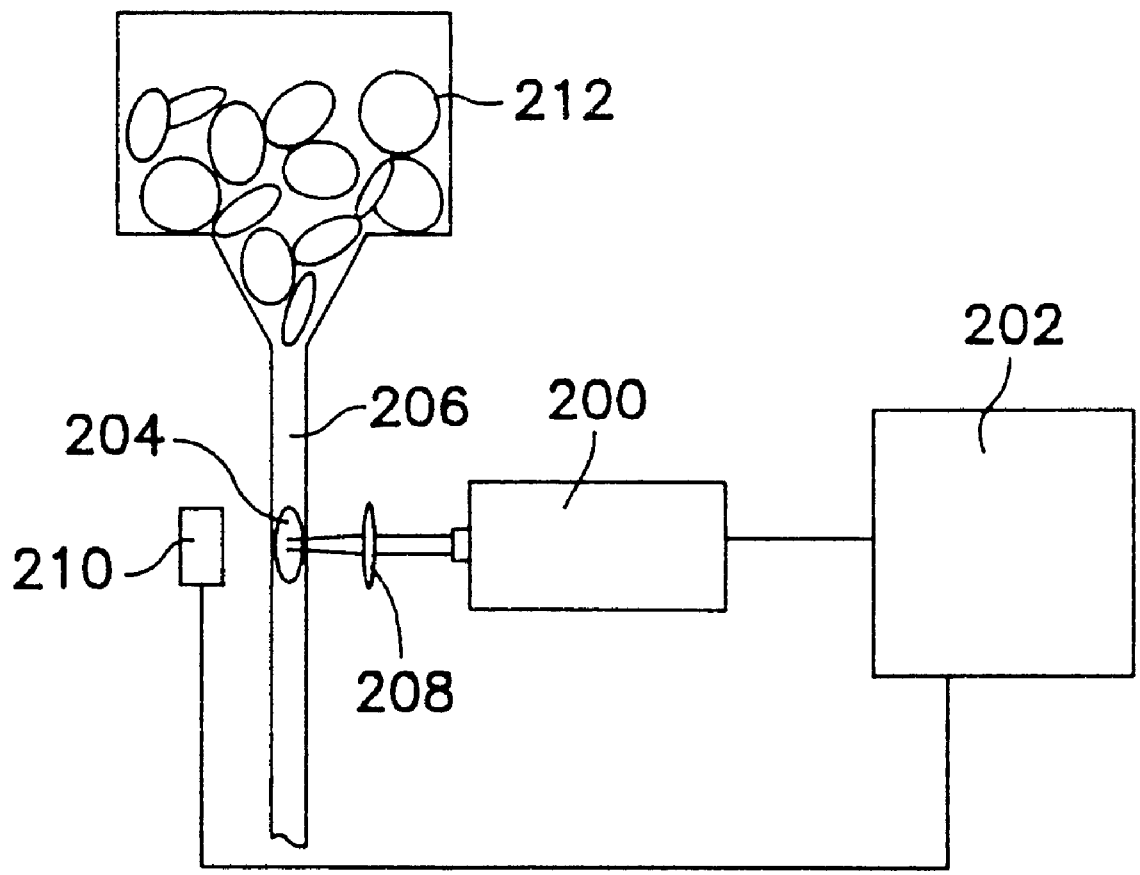
FIG. 8 is an illustration of a second exemplary embodiment of an apparatus for separating matrix particles for individual exposure to an optical signal.

As illustrated In FIG. 8, an optical write/read system is configured similar to that of the embodiment of FIG. 7, with a vessel 212 containing a number of the particles which are separated and oriented by passing through a constricted outlet into a write/read path 206 consisting of an optically-transparent tube with a cross-section which orients the particles as required to expose the memory surface to the laser 200 which is capable of emitting a plurality of discrete, stable wavelengths. Gating and detection similar to that described for the previous embodiment may be used and are not shown. Computer 202 controls the tuning of laser 200 so that it emits light at a unique wavelength to record a data point. Memory within computer 202 stores a record indicating which process step corresponds to which wavelength. For example, for process A, wavelength $\lambda_1$, e.g., 630 nm [red], for process C, $\lambda_2$, e.g., 550 nm [yellow], and for process E, $\lambda_3$, e.g., 480 nm [blue], etc. The recording medium 204 is configured to permit orientation to repeatably expose the recording side of the medium to the laser beam each time it passes through tube 206. One possible configuration, as illustrated here, is a disc.

To write onto the recording medium 204, the laser 200 emits light of the selected wavelength to form a spectral hole in the medium. The light is focused by lens 208 to illuminate a spot on recording medium 204. The laser power must be sufficient to form the spectral hole. For reading, the same wavelength is selected at a lower power. Only this wavelength will pass through the spectral hole, where it is detected by detector 210, which provides a signal to computer 202 indicative of the recorded wavelength. Because different wavelengths are used, multiple spectral holes can be superimposed so that the recording medium can be very small for purposes of tagging. To provide an analogy to the electrical memory embodiments, each different wavelength of light corresponds to an address, so that each laser writes one bit of data. If a large number of different steps are to be performed for which each requires a unique data point, the recording media will need to be sufficiently sensitive, and the lasers well-stabilized, to vary only within a narrow band to assure that each bit recorded in the media is distinguishable. Since only a single bit of information is required to tag the particle at any given step, the creation of a single spectral hole at a specific wavelength is capable of providing all of the information needed. The host computer then makes a record associating the process performed with a particular laser wavelength.

For reading, the same wavelength laser that was used to create the spectral hole will be the only light transmitted through the hole. Since the spectral holes cannot be altered except by a laser having sufficient power to create additional holes, this type of memory is effectively non-volatile. Further, the recording medium itself does not have any operations occurring within its structure, as is the case in electrical memories, so its structure is quite simple. Since the recording medium is photochemically active, it must be well encased within an optically transmissive, inert material to prevent reaction with the various processing substances while still permitting the laser light to impinge upon the medium. In many cases, the photochemical recording media may be erased by exposure to broad spectrum light, allowing the memory to be reused.

Writing techniques can also include the formation of pits in the medium. To read these pits, the detector 210 with be positioned on the same side of the write/read tube 206 as the laser 200 to detect light reflected back from the medium. Other types of optical data storage and recording media may be used as are known in the art. For example, optical discs, which are typically plastic-encapsulated metals, such as aluminum, may be miniaturized, and written to and read from using conventional optical disc technology. In such a system, the miniature discs must be aligned in a planar fashion to permit writing and reading. A modification of the funnel system, described above, will include a flattened tube to insure the proper orientation. Other optical recording media that may be appropriate for use in the recording devices and combinations herein include, but are not limited to, magneto-optical materials, which provide the advantage of erasability, photochromic materials, photoferroelectric materials, photoconductive electro-optic materials, all of which utilize polarized light for writing and/or reading, as is known in the art. When using any form of optical recording, however, considerations must be made to insure that the selected wavelength of light will not affect or interfere with reactions of the molecules or biological particles linked to or in proximity to matrix particles.

C. Preparation of the Combinations

1. Preparation of Matrix-memory Combinations

In preferred embodiments, the recording device is cast in a selected matrix material during manufacture. Alternatively, the devices can be physically inserted into the matrix material, the deformable gel-like materials, or can be placed on the matrix material and attached by a connector, such as a plastic or wax or other such material.

2. Non-linked Matrix-memory Combinations

The recording device with memory can be placed onto the inner surface of a vessel, such as a microtiter plate or vial or tube in which the reaction steps are conducted. Alternatively, the device can be incorporated into the vessel material, such into the a wall of each microtiter well or vial or tube in which the reaction is conducted. As long as the molecules or biological particles remain associated with the well, tube or vial, their identity can be tracked.

3. Preparation of Matrix-memory-molecule or Biological Particle Combinations In certain embodiments, combinations of matrices with memories and biological particle combinations are prepared. For example, libraries can be prepared on the matrices with memories, and stored as such for future use or antibodies can be linked to the matrices with memories and stored for future use.

D. The Systems

Systems for recording and reading information are provided. The systems include a host computer or decoder/encoder instrument, a transmitter, a receiver and the data storage device. The systems also can include a funnel-like device or the like for use in tagging single memory devices. In practice, an EM signal, preferably a radio frequency signal is transmitted to the data storage device. The antenna or other receiver means in the device detects the signal and transmits it to the memory, whereby the data are written to the memory and stored in a memory location.

As discussed above, mixtures of the matrix with memory-linked molecules or biological particles may be exposed to the EM signal, or each matrix with memory [either before, after or during linkage of the biological particles or molecules] may be individually exposed, using a device, such as that depicted herein, to the EM signal. Each matrix with memory, as discussed below, will be linked to a plurality of molecules or biological particles, which may, depending upon the application be identical or substantially identical or a mixture of molecules or biological particles depending upon the application and protocol in which the matrix with memory and linked [or proximate] molecules or biological particles is used. The memory can be programmed with data regarding such parameters.

The location of the data, which when read and transmitted to the host computer or decoder/encoder instrument, corresponds to identifying information about linked or proximate molecules or biological particles. The host computer or decoder/encoder instrument can either identify the location of the data for interpretation by a human or another computer or the host computer or the decoder/encoder can be programmed with a key to interpret or decode the data and thereby identify the linked molecule or biological particle.

E. Applications

The matrices with remotely programmable memory(ies) may be used with any methodology that employs molecules or biological particles linked to or combined with matrices. Examples of such methods include, but are not limited to, methods for synthesis and screening of combinatorial libraries and other libraries, described in the following references: U.S. Pat. Nos. 5,403,750, 5,395,750, 5,395,587, 5,384,261, 5,359,115, 5,348,867, 5,338,665, 5,316,922, 5,223,409, 5,223,408, 5,382,513, 5,260,203, 5,258,289, 5,270,170, 5,288,514, 4,631,211, International Application WO 94/28424, which is based on U.S. application Ser. No. 08/069,352; WO 94/13623, which is based on U.S. application Ser. No. 07/988,278; and International Application WO 94/08051, which is based on U.S. application Ser. Nos. 08/013,948 and 07/955,371, which describes synthetic schemes for preparing libraries. Such methods also include, enzyme immunoassays, particularly ELISAs, which rely on support bound antigens, antibodies or complexes thereof; and assays and methods using hybridizations using solid phase-bound nucleic acids. Support-bound molecules and biological particles are often used in methods of affinity purification. There are innumerable protocols that utilize support-bound ligands of any sort, including support-bound antibodies, and support bound nucleic acids.

Thus, there are many approaches known that rely on combinations of solid phases and molecules or biological particles, and the above listing and following discussion is intended to exemplify, but not limit the methods to which the technology provided herein is applicable.

1. Combinatorial Syntheses

(a) Oligomer and Polypeptide Libraries

(i) Bio-oligomer Libraries

One exemplary method for generating a library [see, U.S. Pat. No. 5,382,513] involves repeating the steps of (1) providing at least two aliquots of a solid phase support; separately introducing a set of subunits to the aliquots of the solid phase support; completely coupling the subunit to substantially all sites of the solid phase support to form a solid phase support/new subunit combination, assessing the completeness of coupling and if necessary, forcing the reaction to completeness; thoroughly mixing the aliquots of solid phase support/new subunit combination; and, after repeating the foregoing steps the desired number of times, removing protecting groups such that the bio-oligomer remains linked to the solid phase support. In one embodiment, the subunit may be an amino acid, and the bio-oligomer may be a peptide. In another embodiment, the subunit may be a nucleoside and the bio-oligomer may be an oligonucleotide. In a further embodiment, the nucleoside is deoxyribonucleic acid; in yet another embodiment, the nucleoside is ribonucleic acid. In a further embodiment, the subunit may be an amino acid or a nucleoside, and the bio-oligomer may be a peptide-oligonucleotide chimera. Each solid phase support is attached to a single bio-oligomer species and all possible combinations of monomer subunits of which the bio-oligomers are composed are included in the collection.

In practicing this method herein, the support matrix has a recording device with programmable memory, encased, linked or otherwise attached to the matrix material, and at each step in the synthesis the support matrix to which the nascent polymer is attached is programmed to record the identity of the subunit that is added. At the completion of synthesis of each biopolymer, the resulting biopolymers linked to the supports are mixed.

After mixing an acceptor molecule or substrate molecule of interest is added. The acceptor molecule is one that recognizes and binds to one or more solid phase matrix with memory/bio-oligomer species within the mixture or the substrate molecule will undergo a chemical reaction catalyzed by one or more solid phase matrix with memory/bio-oligomer species within the library. The resulting combinations that bind to the acceptor molecule or catalyze reaction are selected. The memory in the matrix-memory combination is read and the identity of the active bio-oligomer species is determined.

(ii) Split Bead Sequential Syntheses

Figure 2:
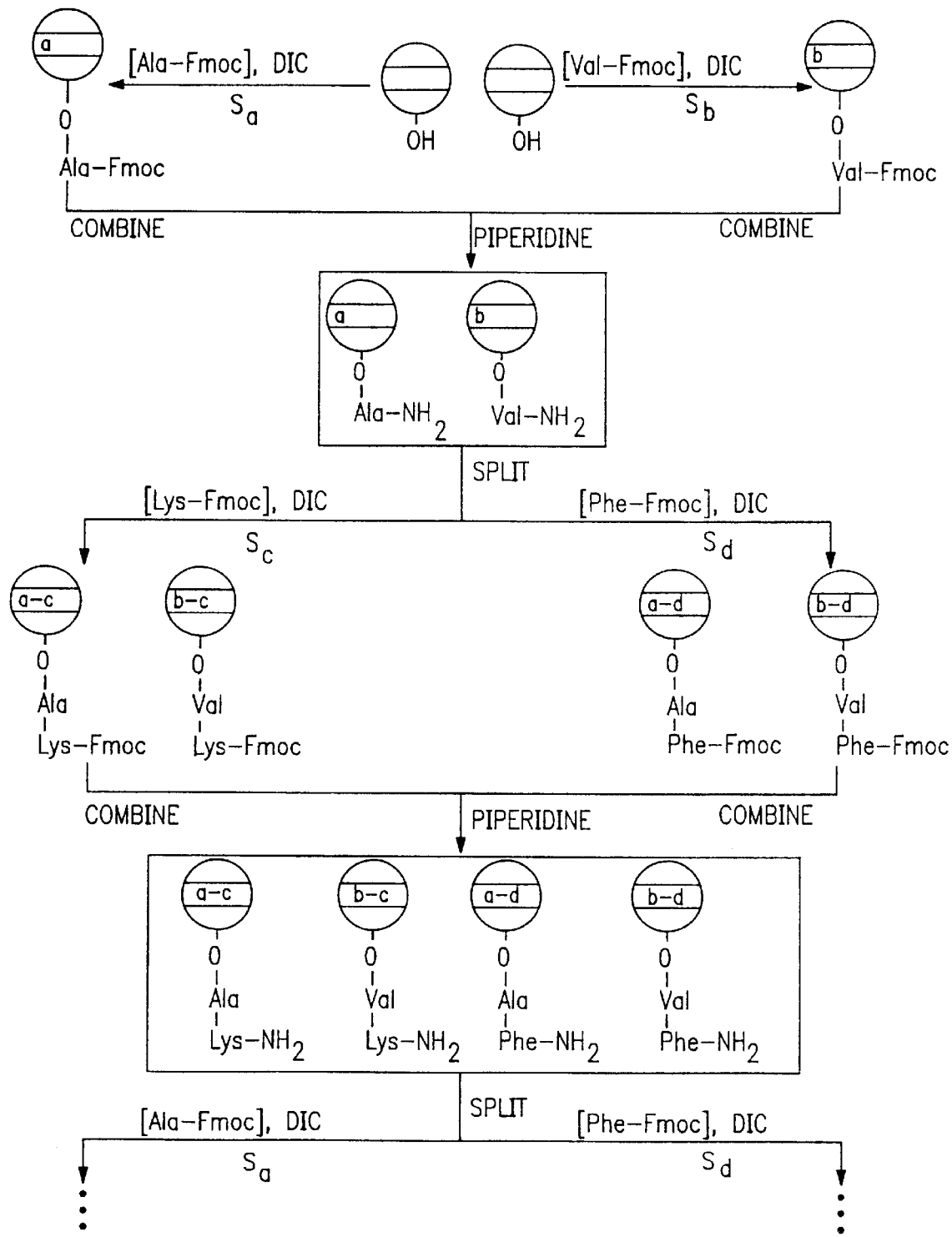
FIG. 2 depicts combinatorial synthesis of peptides on a matrix with memory. Each amino acid has a corresponding code, a, b, c . . . , in the matrix memory.
Figure 3:
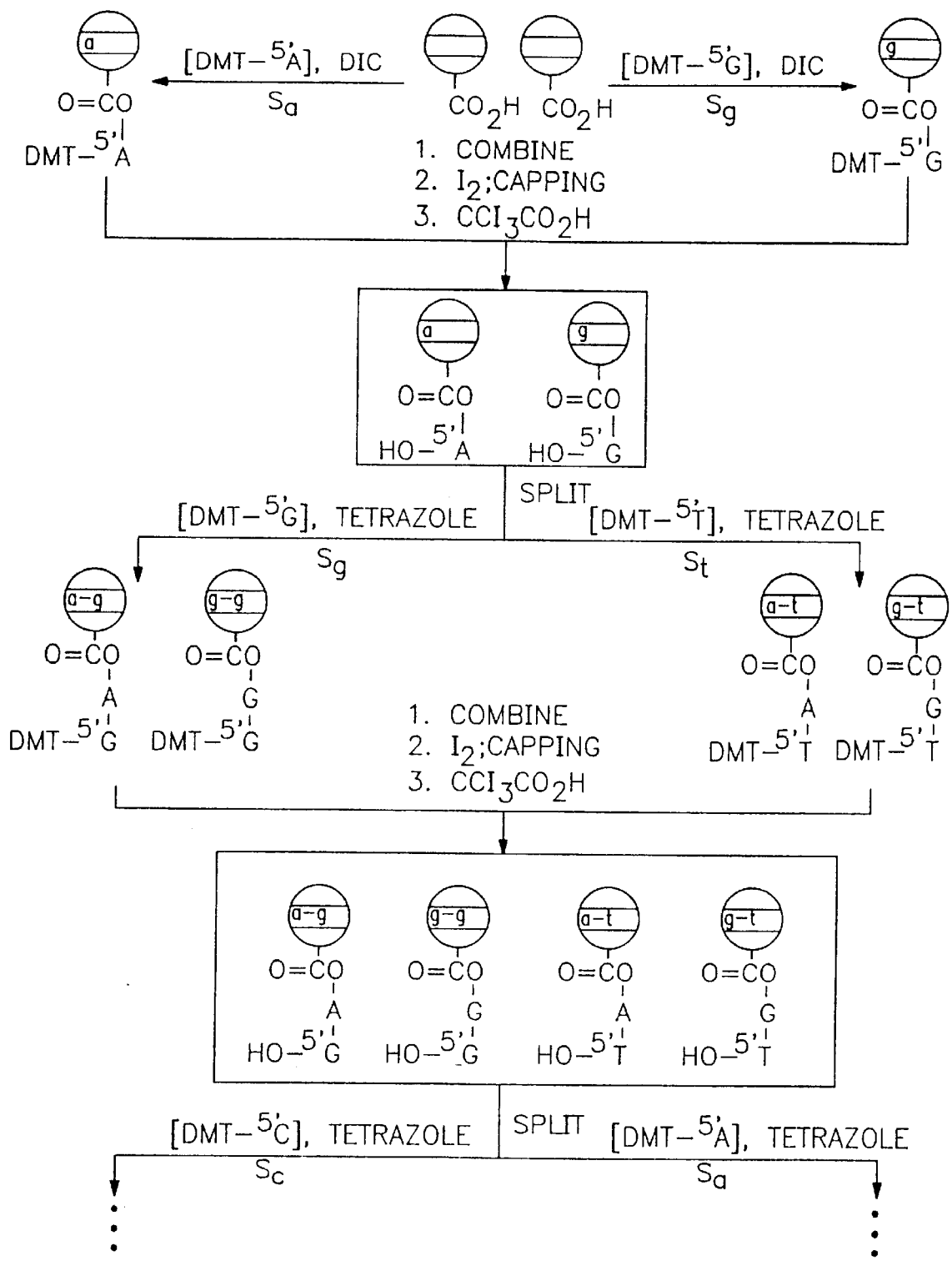
FIG. 3 depicts combinatorial synthesis of oligonucleotides on matrix supports with memories. A, G, T and C represent nucleotides, and a, g, t, and c represent the electronic codes stored in memory that correspond to each of A, G T and C,, respectively. The phosphoramidite method of oligonucleotide synthesis is performed by methods known to those of skill in the art [see, e.g., Brown et al. (1991) "Modern machine-aided methods of oligodeoxyribonucleotide synthesis" in Oligonucleotides Analogues EDITOR: Eckstein, Fritz (Ed), IRL, Oxford, UK., pp. 1–24, esp. pp. 4–7].
Figure 4:
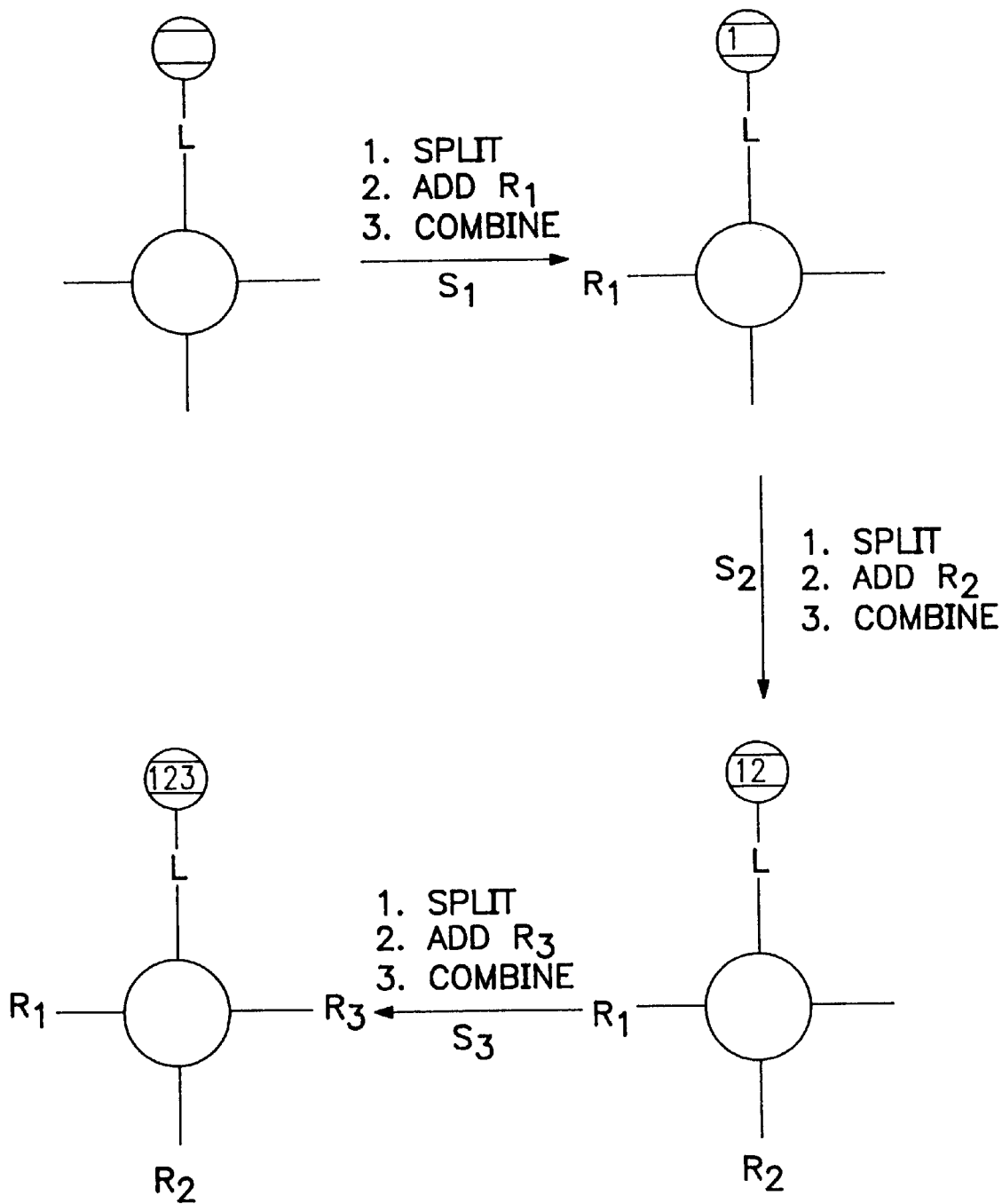
FIG. 4 depicts generation of a chemical library, such as a library of organic molecules, in which $R_1$, $R_2$, $R_3$ are substituents on selected molecule, such as a pharmacophore monomer, each identified with a different signal, depicted as 1, 2, or 3, from the classes $S_1$, $S_2$, $S_3$, respectively. The circle represents an organic pharmacophore. If $R_1$–$R_3$ are the same, and selected from among the same 50 choices, then the complete library contains $50^3 = 125,000$ members. If $R_1$–$R_3$ are selected from among different sets of choices, then the resulting library has correspondingly more members. Each matrix memory can be encoded with information that represents the $R_n$ added and class $[S_n]$ thereby providing a unique code for each library member.

Various schemes for split bead syntheses of polymers [FIG. 1], peptides [FIG. 2], nucleic acids [FIG. 3] and organic molecules based on a pharmacophore monomer [FIG. 4] are provided. Selected matrices with memory particles are placed in a suitable separation, such as a funnel

[see, FIG. 5]. After each synthetic step, each particle is scanned as it passes the RF transmitter, and information identifying the added component or class of components is stored in memory. For each type of synthesis a code can be programmed [i.e., a 1 at position 1,1 in the memory could, for example, represent alanine at the first position in the peptide]. A host computer or decoder/encoder is programmed to send the appropriate signal to a transmitter that results in the appropriate information stored in the memory [i.e, for alanine as amino acid 1, a 1 stored at position 1,1]. When read, the host computer or decoder/encoder can interpret the signal read from and transmitted from the memory.

In an exemplary embodiment, a selected number of beads [i.e., particulate matrices with memories [matrix particles linked to recording devices], typically at least $10^3$, more often $10^4$, and desirably at least $10^5$ or more up to and perhaps exceeding $10^{15}$, are selected or prepared. The beads are then divided into groups, depending upon the number of choices for the first component of the molecule. They are divided into a number of containers equal to or less than [for pooled screening, nested libraries or the other such methods] the number of choices. The containers can be microtiter wells, Merrifield synthesis vessels, columns, test tubes, gels, etc. The appropriate reagents and monomer are added to each container and the beads in the first container are scanned with electromagnetic with radiation, preferably high frequency radio waves, to transmit information and encode the memory to identify the first monomer. The beads in the second container are so treated. The beads are then combined and separated according to the combinatorial protocol, and at each stage of added monomer each separate group is labeled by inputting data specific to the monomer. At the end of the synthesis protocol each bead has an oligomer attached and information identifying the oligomer stored in memory in a form that can be retrieved and decoded to reveal the identity of each oligomer.

(b) "Nested" Combinatorial Library Protocols

In this type of protocol libraries of sublibraries are screened, and a sublibrary selected for further screening [see, e.g., Zuckermann et al. (1994) *J. Med. Chem.* 37:2678–2685; and Zuckermann et al. (1992) *J. Am. Chem. Soc.* 114:10646–10647]. In this method, three sets of monomers were chosen from commercially available monomers, a set of four aromatic hydrophobic monomers, a set of three hydroxylic monomers, a set of seventeen diverse monomers, and three N-termini were selected. The selection was based on an analysis of the target receptor and known ligands. A library containing eighteen mixtures, generated from the six permutations of the three monomer sets, times three N-termini was prepared. Each mixture of all combinations of the three sets of amines, four sets of hydrophobic monomers and seventeen diverse monomers was then assayed. The most potent mixture was selected for deconvolution by synthesis of pools of combinatorial mixtures of the components of the selected pool. This process was repeated, until individual compounds were selected.

Tagging the mixtures with the matrices with memories will greatly simplify the above protocol. Instead of screening each mixture separately, each matrix particle with memory will be prepared with sets of the compounds, analogous to the mixtures of compounds. The resulting matrix particles with memories and linked compounds can be combined and then assayed. As with any of the methods provided herein, the linked compounds [molecules or biological particles] can be cleaved from the matrix with memory prior to assaying or anytime thereafter, as long as the cleaved molecules remain in proximity to the device or in some manner can be identified as the molecules or particles that were linked to the device. The matrix particle (s) with memories that exhibit the highest affinity [bind the greatest amount of sample at equilibrium] are selected and identified by querying the memory to identify the group of compounds. This group of compounds is then deconvoluted and further screened by repeating this process, on or off the matrices with memories, until high affinity compounds are selected.

2. Multianalyte Immunoassays

The combinations of matrix with memories provided herein permits the simultaneous assay of large numbers of analytes in any format. These combinations are particularly suitable for analyses of multianalytes in a fluid, and particularly for multianalyte immunoassays. In one example, monoclonal antibodies very specific for carcinoembryonic antigen [CEA], prostate specific antigen [PSA], CA-125, alphafetoprotein [AFP], TGF-β, IL-2, IL-8 and IL-10 are each covalently attached to a different batch of matrices with memories using well-established procedures and matrices for solid phase antibody assays. Each antibody-matrix with memory complex is given a specific identification tag, as described herein.

A sample of serum from a patient to be screened for the presence or concentration of these antigens is added to a tube containing two of each antibody-matrix with memory complex [a total of 16 beads, or duplicates of each kind of bead]. A mixture of monoclonal antibodies, previously conjugated to fluorescent dyes, such as fluorescein or phenyl-EDTA-Eu chelate, reactive with different epitopes on each of the antigens is then added. The tubes are then sealed and the contents are mixed for sufficient time [typically one hour] to allow any antigens present to bind to their specific antibody-matrix with memory-antigen complex to produce antibody-matrix with memory-antigen-labeled antibody complexes. At the end of the time period, these resulting complexes are briefly rinsed and passed through an apparatus, such as that set forth in FIG. 7, but with an additional light source. As each complex passes through a light source, such as a laser emitting at the excitation wavelength of fluorescein, about 494 nm, or 340 nm for the Eu chelate complex, its fluorescence is measured and quantitated by reading the emitted photons at about 518 nm for fluorescein or 613 nm for phenyl-EDTA-Eu, and as its identity is determined by the specific signal received by the RF detector. In this manner, eight different antigens are simultaneously detected and quantitated in duplicate.

In an embodiment, the electromagnetically tagged matrices to record information regarding linked antibodies can be used with other multianalyte assays, such as those described by Ekins et al. [(1990) *J. Clin. Immunoassay* 13:169–181]. These methods rely on the use of small concentrations of sensor-antibodies within a few $\mu m^2$ area. Individual memories with matrices, or an array of memories embedded in a matrix are used. Different antibodies are linked to each memory, which is programmed to record the identity of the linked antibody. Alternatively, the antibody can be linked, and its identity or binding sites identified, and the information recorded in the memory.

In particular antibodies are linked to the matrices with memories. The matrices are either in particular form or in the form of a slab with an array of recording devices linked to the matrices or microtiter dish or the like with a recording device in each well. Antibodies are then linked either to each matrix particle or to discrete "microspots" on the slab or in the microtiter wells. In one application, prior to use of these matrices with memories, they are bound to a relatively low affinity anti-idiotype antibody labeled with a fluorophore [e.g., Texas Red, see, Ekins et al. (1990) *J. Clin. Immunoassay* 13:169–181] to measure the concentration of and number of available binding sites present on each matrix with memory particle or each microspot, which information is then encoded into each memory for each microspot or each particle. These low affinity antibodies are then eluted, and the matrices can be dried and stored until used. They can be used for multianalyte analyses as described above.

After reaction with the test sample, the matrices with memories are reacted with a second antibody, preferably labeled with a different label, such as a different fluorophore, such as fluorescein. After this incubation, the microspots or each matrix particle is read by passing the particle through a laser scanner [such as a confocal microscope, see, e.g., Ekins et al. (1990) *J. Clin. Immunoassay* 13:169–181; see also U.S. Pat. No. 5,342,633] to determine the fluorescence intensity. The memories at each spot or linked to each particle are queried to determine the total number of available binding sites, thereby permitting calculation of the ratio of occupied to unoccupied binding sites.

Alternatively or additionally, the memories in the particles or at each microspot could be programmed with the identity or specificity of the linked antibody, so that after reaction with the test sample and identification of complexed antibodies, the presence and concentration of particular analytes in the sample can be determined.

3. Phage Display

Phage, viruses, bacteria and other such manipulable hosts and vectors [referred to as biological particles] can be modified to express selected antigens on their surfaces by, for example, inserting DNA encoding the antigen into the host or vector genome, at a site such as in the DNA encoding the coat protein, such that upon expression the antigen is presented on the surface of the virus, phage or bacterial host. Libraries of such packages that express diverse or families of proteins on their surfaces have been prepared. The resulting library is then screened with a targeted antigen and those with the highest affinity for the antigen are selected [see, e.g., U.S. Pat. Nos. 5,403,484, 5,395,750, 5,382,513, 5,316,922, 5,288,622, 5,223,409, 5,223,408 and 5,348,867]. For example, libraries of synthetic antigens expressed on the surfaces of such packages have been prepared.

DNA molecules, each encoding proteins containing a family of similar potential binding domains and a structural signal calling for the display of the protein on the outer surface of a selected viral or bacterial or other package, such as a bacterial cell, bacterial spore, phage, or virus are introduced into the bacterial host, virus or phage. The protein is expressed and the potential binding domain is displayed on the outer surface of the package. The cells or viruses bearing the binding domains to which target molecules bind are isolated and amplified, and then are characterized. One or more of these successful binding domains is used as a model for the design of a new family of potential binding domains, and the process is repeated until a novel binding domain having a desired affinity for the target molecule is obtained. For example, libraries of de novo synthesized synthetic antibody library containing antibody fragments expressed on the surface have been prepared. DNA encoding synthetic antibodies, which have the structure of antibodies, specifically Fab or Fv fragments, and contain randomized binding sequences that may correspond in length to hypervariable regions [CDRs] can be inserted into such vectors and screened with an antigen of choice.

An immunoglobulin contains heavy and light chains that each contain variable and constant domains. The smallest antibody fragment that forms an antigen binding site is referred to as an Fv fragment. These Fv fragments have been prepared, using genetic engineering methods, such that they contain the heavy and light chain variable regions tethered together by a linker, such as a flexible glycine-serine (gly-ser)$_n$, in which n is 1 or more, typically 3 or 4 or more. The variable regions can be further subdivided into framework regions that are fairly well conserved among antibodies and hypervariable regions [CDR] that are quite diverse and are important in defining antigen specificity.

Synthetic antibody libraries can be manipulated and modified for use in combinatorial type approaches in which the heavy and light chain variable regions are shuffled and exchanged between synthetic antibodies in order to affect specificities and affinities. This enables the production of antibodies that bind to a selected antigen with a selected affinity. The approach of constructing synthetic single chain antibodies is directly applicable to constructing synthetic Fab fragments which can also be easily displayed and screened. The diversity of the synthetic antibody libraries can be increased by altering the chain lengths of the CDRs and also by incorporating changes in the framework regions that may affect antibody affinity. In addition, alternative libraries can be generated with varying degrees of randomness or diversity by limiting the amount of degeneracy at certain positions within the CDRs. The synthetic library can be modified further by varying the chain lengths of the CDRs and adjusting amino acids at defined positions in the CDRs or the framework region which may affect affinities. Antibodies identified from the synthetic antibody library can easily be manipulated to adjust their affinity and or effector functions. In addition, the synthetic antibody library is amenable to use in other combinatorial type approaches. Also, nucleic acid amplification techniques have made it possible to engineer humanized antibodies and to clone the immunoglobulin [antibody] repertoire of an immunized mouse from spleen cells into phage expression vectors and identify expressed antibody fragments specific to the antigen used for immunization [see, e.g., U.S. Pat. No. 5,395,750].

The antigens, particularly mixtures thereof, used in screening can be coupled to a solid matrix that has been combined with a recording device containing an programmable PROM or EEPROM or immobilized in micotiter plates containing such devices or in a resin, such as an Affigel® resin, containing such device [any of the preceding are matrices with memories] for use in screening antibody phage [phagemids, or PAL fusion bacteria].

Alternatively, the phage or other package can be prepared in batches and are linked to matrices that identify the DNA that has been inserted into the phage. The matrices are then mixed and screened with labeled antigen [e.g., fluorescent or enzymatically] or hapten, using an assay carried out with limiting quantities of the antigen, thereby selecting for higher affinity phage. Thus, libraries of phage linked to matrix particles with memories can be prepared. The matrices are encoded to identify the batch number of the phage, a sublibrary, or to identify a unique sequence of nucleotides or amino acids in the antibody or antibody fragment expressed on its surface. The library is then screened with labeled antigens. The antigens are labeled with enzyme labels or radiolabels or with the antigen bound with a second binding reagent, such as a second antibody specific for a second epitope to which a fluorescent antigen binds.

Following identification of antigen bound phage, the matrix particle can be queried and the identity of the phage determined. The resulting information represents a profile of the sequence that binds to the antigen. This information can be analyzed using methods known to those of skill in this art.

4. Selection of Antibodies

After cloning and plating of cells [fusion cells] that secrete antibodies "panning" for the desired monoclonal or polyclonal among a vast mixture of antibodies is a time consuming and laborious process. Attaching antibody-binding epitopes to the matrix particle with memory and "panning" with a vast number of matrix particles with memories linked to amino acids forming different epitopes or to phage particles expressing different epitopes would greatly facilitate the isolation of desired clones. After screening with the mixture of epitopes, the specificity of the selected antibodies could be determined by querying each memory.

Alternatively, the fused cells are plated into, for example, microtiter wells with the matrices with memory-tagged antibody binding reagent [such as protein A]. The solid phase is removed, pooled and processed batchwise to identify the cells that produce antibodies that are the greatest binders [see, e.g., U.S. Pat. No. 5,324,633 for methods and device for measuring the binding affinity of a receptor to a ligand].

5. Hybridization Assays

Mixtures of nucleic acid probes linked to the matrices with memories can be used for screening in assays that heretofore had to be done with one probe at a time or with mixtures of probes followed by sequencing the hybridizing probes. There are numerous examples of such assays [see, e.g., U.S. Pat. No. 5,292,874, "Nucleic acid probes to *Staphylococcus aureus*" to Milliman, and U.S. Pat. No. 5,232,831, "Nucleic acid probes to *Streptococcus pyogenes*" to Milliman, et al.; see, also, U.S. Pat. Nos. 5,216,143, 5,284,747 5,352,579 and 5,374,718]. For example, U.S. Pat. No. 5,232,831 provides probes for the detection of particular Streptococcus species from among related species and methods using the probes. These probes are based on regions of Streptococcus rRNA that are not conserved among related Streptococcus species. Particular species are identified by hybridizing with mixtures of probes and ascertaining which probe(s) hybridize. By virtue of the instant matrices with memories, following hybridization, the identity of the hybridizing probes can be determined by querying the memories, and thereby identifying the hybridizing probe.

6. Natural Product Screening

In the past, the vast majority of mainline pharmaceuticals have been isolated form natural products such as plants, bacteria, fungus, and marine microorganisms. Some of these compounds include enzymes [e.g., hyaluronidase], industrial chemicals [e.g., petroleum emulsifying agents], and antibiotics [e.g., penicillin]. It is generally considered that a wealth of new agents still exist within the natural products pool. Large mixtures of natural products, even within a fermentation broth, can be screened using the matrices with memory combinations linked, for example, to peptides, such as antigens or antibody fragments, of selected and known sequences. Mixtures of these peptides linked to memory matrices can be introduced into the natural product mixture. Individual binding matrices, detected by an indicator, such as a fluorometric dye, can be isolated and the memory queried to determine which linked molecule or biological particle is bound to a natural product.

7. Separations, Physical Mapping and Measurements of Kinetics of Binding and Binding Affinities Multiple blots may be simultaneously reacted and processed. Each memory, preferably in the form of a rectangle, is linked or coated on one surface with material, such as nitrocellose, to which or the analyte of interest binds or with which it reacts. The chips are arranged in an array, preferably rectangular, and the respective x-y coordinate or other position-identifying coordinate or, and, if needed, sheet number, is programmed into each memory. The are preferably linked together, such as by glue, or placing them in agarose, as long as the reactive surface is not disturbed. Following transfer of the material, such as transfer of protein from a Western Blot, or nucleic acid from a Southern or Northern blot, the memories are separated and mixed for reaction with a traditionally labeled, such as a fluorescent label, detection nucleic acid, protein, or antibody. Complexes are identified, and their origin in the blot determined by retrieving the stored information in each chip. Quantitation may also be effected based on the amount of label bound.

Such support bound analytes may also be used to analyze the kinetics of binding by continuously passing the supports through a label reading device during the reaction, and identify the labeled complexes. The binding agents can be eluted, either in a kinetically readable manner or in batch. After elution, the support bound analytes may be identified to analyze kinetics of binding to the binding agent. Such binding and elution protocols may also be adapted to affinity purification methodologies.

Since modifications will be apparent to those of skill in this art, it is intended that this invention be limited only by the scope of the appended claims.

What is claimed:

1. A method for electromagnetically tagging molecules or biological particles, comprising contacting the molecules or biological particles with a combination of a matrix with memory, wherein:

the combination of a matrix with memory comprises:
(A) a remotely addressable recording device, comprising a data storage unit; and
(B) a matrix material, wherein:
the matrix material is in the form of a container used for chemical syntheses that has a volume of about 100 ml or less;
the recording device is in contact with the matrix or in a solution that is in contact with the matrix; and
the contacting is effected by placing the molecules or biological particles in proximity to the combination or by placing the combination in physical contact with the molecules or biological particles.

2. A method for electromagnetically tagging molecules or biological particles, comprising:

contacting the molecules or biological particles with a recording device, comprising an antifuse memory means for storing a plurality of data points and means for receiving a transmitted electromagnetic signal so that a write signal causes a stored data point corresponding to the data signal to be stored within the memory means; and transmitting an electromagnetic signal to the device, whereby a data point is stored within the memory means.

3. The method of claim 2, wherein the process of contacting and transmitting of a data point is repeated a plurality of times with additional molecules or biological particles and recording devices to produce a plurality of electronically tagged molecules or biological particles.

4. The method of claim 2, wherein the process is automated.

5. A method for electromagnetically tagging a support matrix, comprising contacting the matrix with a recording device, wherein:

the contact may be direct or may be effected indirectly;

the recording device includes a non-volatile memory means for storing a plurality of data points and means for receiving a transmitted electromagnetic signal so that a write signal causes a stored data point corresponding to the data signal to be stored within the non-volatile memory means;

and the non-volatile memory means comprises an antifuse.

6. A method for electromagnetically tagging a support matrix, comprising contacting the matrix with a recording device, wherein:

the recording device, comprises a memory device having an optical recording medium for storing a plurality of data points and means for receiving a projected optical signal having a first intensity for forming a plurality of spectral holes in the optical recording medium, wherein each spectral hole of the plurality of spectral holes corresponds to a stored data point.

7. The method of claim 6, wherein the projected optical signal comprises a second intensity for reading the stored data point by detecting the presence of each spectral hole in the optical recording medium.

8. A method for identifying or tracking molecules and biological particles, comprising:

(a) providing at least one recording device that is linked to, in contact with, or in proximity to, a molecule or biological particle;

(b) programming the recording device with
(i) one or more indicators representative of the identity of the molecule or biological particle, and/or
(ii) one or more indicators representative of physical or chemical properties of the molecule or biological particle;
wherein the recording device comprises an antifuse, or the recording device comprises an optical recording medium;

(c) retrieving the at least one recording device and linked, contacted or proximate molecule or biological particle and reading stored information, thereby determining the identity of and tracking the molecule or biological particle linked, contacted or proximate to the recording device.

9. The method of claim 8, further comprising:

exposing the recording device to electromagnetic radiation; and transmitting to a host computer or decoder/encoder instrument the indicator(s) representative of the identity of the molecule or biological particle, or physical or chemical properties of the molecule or biological particle, or other identifying information for tracking the molecule or biological particle.

10. An array, comprising a substantially continuous sheet and a plurality of combinations of a matrix with memory wherein:

each combination of a matrix with memory comprises:
(A) matrix material; and
(B) a recording device that is coated on at least one side with matrix material and that comprises a data storage unit, wherein:
the matrix material is either comprised of particles of a size such that at least one dimension is no more than 100 mm or the matrix material is in the form of a container used for chemical syntheses;
the matrix material is fabricated from material that can be used as a support matrix in chemical syntheses and reactions;
each recording device includes a data storage unit with remotely programmable or readable memory capable of storage of multiple bits of data; and
each device is programmed with data identifying the relative position of each combination in the array.

11. The array of claim 10, wherein the device is less than about 10 mm$^3$ in size.

12. The array of claim 10, wherein each combination is contiguous to the adjacent combination, whereby a continuous matrix surface is formed.

13. The array of claim 10, wherein the matrix comprises nitrocellulose.

14. In a Southern, Northern, Western or dot blot assay, the improvement comprising, linking the blot to a plurality of data storage devices, wherein the relative position in the blot of each data storage device is programmed into the data storage device.

15. The assay of claim 14, wherein:

the blot is comprised of an array containing a plurality of combinations of a matrix with memory;

the combination of a matrix with memory, comprises:
(A) a recording device, comprising an electromagnetically remotely programmable data storage unit; and
(B) a matrix material coating at least one side of the device; and the array contains a contiguous arrangement of the combinations, whereby a continuous blotting surface is formed.

16. The method of claim 1, wherein the container has a volume of 10 ml or less.

17. The method of claim 1, wherein the container is a microtiter plate, a vial or a test tube, a column used in chromatographic separations and purifications or a vessel used for peptide or oligonucleotides syntheses.

18. The method of claim 1, wherein the container is a column used in chromatographic separations and purifications or a vessel used for peptide or oligonucleotides syntheses.

19. The method of claim 1, wherein the device is less than about 10 mm$^3$ in size.

* * * * *